US007129049B2

(12) United States Patent
Valberg et al.

(10) Patent No.: US 7,129,049 B2
(45) Date of Patent: Oct. 31, 2006

(54) METHOD OF DETECTING EQUINE GLYCOGEN STORAGE DISEASE IV

(75) Inventors: Stephanie J. Valberg, Lino Lakes, MN (US); James R. Mickelson, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 337 days.

(21) Appl. No.: 10/746,270

(22) Filed: Dec. 22, 2003

(65) Prior Publication Data

US 2005/0136415 A1    Jun. 23, 2005

(51) Int. Cl.
C07H 21/04    (2006.01)
C12Q 1/68    (2006.01)
(52) U.S. Cl. .................... 435/6; 435/91.1; 435/91.2; 536/23.1; 536/24.3
(58) Field of Classification Search ............... None
See application file for complete search history.

(56) References Cited

U.S. PATENT DOCUMENTS

| | | | |
|---|---|---|---|
| 3,450,819 | A | 6/1969 | Babayan et al. |
| 4,683,195 | A | 7/1987 | Mullis et al. |
| 4,683,202 | A | 7/1987 | Mullis et al. |
| 4,800,159 | A | 1/1989 | Mullis et al. |
| 4,873,192 | A | 10/1989 | Kunkel |
| 4,962,032 | A | 10/1990 | Yoshida et al. |
| 4,965,188 | A | 10/1990 | Mullis et al. |
| 5,460,942 | A | 10/1995 | Chou et al. |
| 5,817,634 | A | 10/1998 | Meezan et al. |
| 5,831,037 | A | 11/1998 | Ohsuga et al. |
| 6,054,587 | A | 4/2000 | Reddy et al. |
| 6,110,903 | A | 8/2000 | Kasibhatla et al. |
| 6,268,471 | B1 | 7/2001 | Romeo |
| 6,284,748 | B1 | 9/2001 | Dang et al. |
| 6,328,958 | B1 | 12/2001 | Amalfitano et al. |
| 6,489,476 | B1 | 12/2002 | Dang et al. |
| 6,500,418 | B1 | 12/2002 | Dieckgraefe et al. |
| 6,610,290 | B1 | 8/2003 | Podsakoff et al. |
| 6,617,104 | B1 | 9/2003 | Swift |
| 2001/0027250 | A1 | 10/2001 | Mariniuk |
| 2002/0040014 | A1 | 4/2002 | Bookser et al. |
| 2002/0102737 | A1 | 8/2002 | Millington et al. |
| 2002/0110551 | A1 | 8/2002 | Chen |
| 2002/0111291 | A1 | 8/2002 | Brown et al. |
| 2002/0173490 | A1 | 11/2002 | Jiang et al. |
| 2003/0035801 | A1 | 2/2003 | Dieckgraefe et al. |
| 2003/0060415 | A1 | 3/2003 | Hung |
| 2003/0091543 | A1 | 5/2003 | Klein et al. |
| 2003/0091553 | A1 | 5/2003 | Gehlsen |
| 2003/0092019 | A1* | 5/2003 | Meyer et al. .............. 435/6 |
| 2003/0095952 | A1 | 5/2003 | Krause et al. |
| 2003/0109010 | A1 | 6/2003 | Fuertes et al. |
| 2003/0109472 | A1 | 6/2003 | Amalfitano et al. |
| 2003/0113762 | A1 | 6/2003 | Warrington |
| 2003/0165462 | A1 | 9/2003 | Amalfitano et al. |
| 2003/0198970 | A1 | 10/2003 | Roberts |

FOREIGN PATENT DOCUMENTS

EP    0 332 435    10/1999

OTHER PUBLICATIONS

Ward et al. Cytogenetic, Genome Research, vol. 102, pp. 201-206, 2003.*
Hirshhorn et al. (Genetics in Medicine. vol. 4, No. 2, pp. 45-61, Mar. 2002).*
Ioannidis (Nature Genetics, vol. 29, pp. 306-309, Nov. 2001).*
GenBank Accession No. AY439007 dated Nov. 12, 2003.
GenBank Accession No. AY505107 dated Aug. 30, 2004.
GenBank Accession No. AY505109 dated Aug. 30, 2004.
GenBank Accession No. AY505110 dated Aug. 30, 2004.
GenBank Accession No. BG835446 dated May 25, 2001.
GenBank Accession No. NM_000158 dated Oct. 26, 2004.
GenBank Accession No. NM_028803 dated Aug. 25, 2004.
GenBank Accession No. XM_221747 dated Oct. 24, 2003.
Altschul et al., "Basic Local Alignment Search Tool," *J. Mol. Biol.*, 1990, 215:403-410.
Altschul et al., "Gapped BLAST and PSI-BLAST: a new generation of protein database search programs," *Nucl. Acids Res.*, 1997, 25(17):3389-3402.
Andersen, "Familial Cirrhosis of the Liver with Storage of Abnormal Glycogen," *Lab. Invest.*, 1956, 5(1):11-20.
Bao et al., "Hepatic and Neuromuscular Forms of Glycogen Storage Disease Type IV Caused by Mutations in the Same Glycogen-branching Enzyme Gene," *J. Clin. Invest.*, 1996, 97(4):941-948.
Batzer et al., "Enhanced evolutionary PCR using oligonucleotides with inosine at the 3'-terminus," *Nucl. Acids Res.*, 1991, 19(18):5081.
Brown and Brown, "Lack of an $\alpha$-1,4-Glucan:$\alpha$-1,4-Glucan 6-Glycosyl Transerase in a Case of Type IV Glycogenosis," *Proc. Natl. Acad. Sci. USA.*, 1966, 56:725-729.
Bruno et al., "Glycogen Branching Enzyme Deficiency in Adult Polyglucosan Body Disease," *Ann. Neurol.*, 1993, 33:88-93.
Cariello et al., "Resolution of a Missense Mutant in Human Genomic DNA by Denaturing Gradient Gel Electrophoresis and Direct Sequencing Using In Vitro DNA Amplification: $HPRT_{Munich}$," *Am. J. Hum. Genet.*, 1988, 42:726-734.
Chee et al., "Accessing Genetic Information with High-Density DNA Arrays," *Science*, 1996, 274:610-614.
Chen, "Glycogen Storage Diseases," *The Metabolic and Molecular Bases of Inherited Disease*, 8th edition, 2001, Scriver et al. (eds.), McGraw-Hill, Inc., New York, Chapter 71, pp. 1521-1551.
Conner et al., "Detection of sickle cell $\beta^S$-globin allele by hybridization with synthetic oligonucleotides," *Proc. Natl. Acad. Sci. USA*, 1983, 80:278-282.
Corpet et al., "Multiple sequence alignment with hierarchical clustering," *Nucl. Acids Res.*, 1988, 16(22):10881-10890.
Cotton et al., "Reactivity of cytosine and thymine in single-base-pair mismatches with hydroxylamine and osmium tetroxide and its application to the study of mutations," *Proc. Natl. Acad. Sci. USA*, 1988, 85:4397-4401.

(Continued)

Primary Examiner—Jeanine A. Goldberg
(74) Attorney, Agent, or Firm—Viksnins Harris & Padys PLLP

(57) ABSTRACT

The present invention relates to diagnosing glycogen storage diseases in mammals.

20 Claims, 4 Drawing Sheets

OTHER PUBLICATIONS de La Blanchardière et al., "Severe Cardiomyopathy Revealing Type IV Glycogen Storage Disease in Two Sibs," *Presse Med.*, 1994, 23:1124-1127.

DiMauro and Lamperti, "Muscle Glycogenoses," *Muscle and Nerve*, 2001, 24:984-999.

Elghanian et al., "Selective Colorimetric Detection of Polynucleotides Based on the Distance-Dependent Optical Properties of Gold Nanoparticles," *Science*, 1997, 277:1078-1081.

Finkelstein et al., "Use of Denaturing Gradient Gel Electrophoresis for Detection of Mutation and Prospective Diagnosis in Late Onset Ornithine Transcarbamylase Deficiency," *Genomics*, 1990, 7:167-172.

Fyfe et al., "Feline glycogenosis type IV is caused by a complex rearrangement deleting 6 kb of the branching enzyme gene and eliminating an exon," *Am. J. Hum. Genet.*, 1997, 61(4):A251, Abstract No. 1457.

Fyfe et a., "Animal Model of Human Disease. Glycogen Storage Disease Type IV," *Comp. Path. Bull.* 1994, 26:3, 6.

Fyfe et al., "Glycogen Storage Disease Type IV: Inherited Deficiency of Branching Enzyme Activity in Cats," *Pediatr. Res.*, 1992, 32(6):719-725.

Goh et al., "Hierarchical pooling and PCR screening of segment 1 of the CHORI 241 equine BAC library," *Proceedings of the Plant & Animal Genome Conference XI*, 2003, San Diego, CA, Abstract No. P637.

Goeddel, "Systems for Heterologous Gene Expression," *Meth. Enzymol.*, 1990, 185:3-7.

Greene et al., "Juvenile Polysaccharidosis With Cardioskeletal Myopathy," *Arch. Pathol. Lab. Med.*, 1987, 111:977-982.

Grompe et al., "Scanning detection of mutations in human ornithine transcarbamoylase by chemical mismatch cleavage," *Proc. Natl. Acad. Sci. USA*, 1989, 86:5888-5892.

Grompe, "The rapid detection of unknown mutations in nucleic acids," *Nat. Genet.*, 1993, 5:111-117.

Guatelli et al., "Isothermal, *in virtro* amplification of nucleic acids by a multienzyme reaction modeled after retroviral replication," *Proc. Natl. Acad. Sci. USA*, 1990, 87:1874-1878.

Hacia et al., "Detection of heterozygous mutations in *BRCA1* using high density oligonucleotide arrays and two-colour fluorescence analysis," *Nat. Genet.*, 1996, 14:441-447.

Higgins and Sharp, "Fast and sensitive multiple sequence alignments on a microcomputer," *CABIOS*, 1989, 5(2):151-153.

Higgins and Sharp, "CLUSTAL: a package for performing multiple sequence alignment on a microcomputer," *Gene*, 1988, 73:237-244.

Huang et al., "Parallelization of a local similarity algorithm," *CABIOS*, 1992, 8(2):155-165.

Karlin and Altschul, "Methods for assessing the statistical significance of molecular sequence features by using general scoring schemes," *Proc. Natl. Acad. Sci. USA*, 1990, 87:2264-2268.

Karlin and Altschul, "Applications and statistics for multiple high-scoring segments in molecular sequences," *Proc. Natl. Acad. Sci. USA*, 1993, 90:5873-5877.

Kinzler et al., "Identification of a Gene Located at Chromosome 5q21 That is Mutated in Colorectal Cancers," *Science*, 1991, 251:1366-1370.

Kunkel et al., "Rapid and Efficient Site-Specific Mutagenesis without Phenotypic Selection," *Meth. Enzymol.*, 1987, 154:367-382.

Kunkel, "Rapid and efficient site-specific mutagenesis without phenotypic selection," *Proc. Natl. Acad. Sci. USA*, 1985, 82:488-492.

Kwoh et al., "Transcription-based amplification system and detection of amplified human immunodeficiency virus type 1 with a bead-based sandwich hybridization format," *Proc. Natl. Acad. Sci. USA*, 1989, 86:1173-1177.

Lewis, "PCRs Competitors Are Alive and Well and Moving Rapidly Towards Commercialization," *Genetic Engineering News*, 1992, 12:1-3.

Lipshutz et al., "Using Oligonucleotide Probe Arrays To Access Genetic Diversity," *BioTechniques*, 1995, 19(3):442-447.

Lizardi et al., "Exponential Amplification of Recombinant-RNA Hybridization Probes," *Bio/Technology*, 1988, 6:1197-1202.

Lockhart et al., "Expression monitoring by hybridization to high-density oligonucleotide arrays," *Nature Biotechnology*, 1996, 14:1675-1680.

Meinkoth and Wahl, "Hybridization of Nucleic Acids Immobilized on Solid Suppots," *Anal. Biochem.*, 1984, 138:267-284.

Mercier and Whelan, "The Fine Structure of Glycogen from Type IV Glcogen-Storage Disease," *Eur. J. Biochem.*, 1970, 16(3):579-583.

Modrich, "Mechanisms and Biological Effects of Mismatch Repair," *Annu. Rev. Genet.*, 1991, 25:229-253.

Moses and Parvari, "The Variable Presentations of Glycogen Storage Disease Type IV: A Review of Clinical, Enzymatic and Molecular Studies," *Curr. Mol. Med.*, 2002, 2:177-188.

Myers and Miller, "Optimal alignments in linear space," *CABIOS*, 1988, 4(1):11-17.

Needleman and Wunsch, "A General Method Applicable to the Search for Similarities in the Amino Acid Sequence of Two Proteins," *J. Mol. Biol.*, 1970, 48:443-453.

Newton et al., "Analysis of any point mutation in DNA. The amplification refractory mutation system (ARMS)," *Nucl. Acids Res.*, 1989, 17:2503-2516.

Nielsen et al., "Sequence-Selective Recognition of DNA by Strand Displacement with a Thymine-Substituted Polyamide," *Science*, 1991, 254:1497-1500.

Novack et al., "Detection of single base-pair mismatches in DNA by chemical modification followed by electrophoresis in 15% polyacrylamide gel," *Proc. Natl. Acad. Sci. USA*, 1986, 83:586-590.

Ohtsuka et al., "An Alternative Approach to Deoxyoligonucleotides as Hybridization Probes by Insertion of Deoxyinosine at Ambiguous Codon Positions," *J. Biol. Chem.*, 1985, 260(5):2605-2608.

Orita et al., "Detection of polymorphisms of human DNA by gel electrophoresis as single-strand conformation polymorphisms," *Proc. Natl. Acad. Sci. USA*, 1989, 86:2766-2770.

Pearson and Lipman, "Improved tools for biological sequence comparison," *Proc. Natl. Acad. Sci. USA*, 1988, 85:2444-2448.

Pearson et al., "Using the FASTA Program to Search Protein and DNA Sequence Databases," *Meth. Mol. Biol.*, 1994, 24:307-331.

Pellissier et al., "Polysaccharide (Amylopectin-like) Storage Myopathy Histochemical, Ultrastructural and Biochemical Studies," *Acta. Neuropath. (Berl)*, 1981, Suppl. VII:292-296.

Ruano and Kidd, "Direct haplotyping of chromosomal segments from multiple heterozygotes via allele-specific PCR amplification," *Nucl. Acids Res.*, 1989, 17(20):8392.

Render et al., "Amylopectinosis in Fetal and Neonatal Quarter Horses," *Vet. Pathol.*, 1999, 36:157-160.

Rossolini et al., "Use of deoxyinosine-containing primers vs degenerate primers for polymerase chain reaction based on ambiguous sequence information," *Mol. Cell. Probes*, 1994, 8:91-98.

Rudolph et al., "Periodic paralysis in Quarter Horses: a sodium channel mutation disseminated by selective breeding," *Nat. Genet.*, 1992, 2:144-147.

Santschi et al., "Endothelin receptor B polymorphism associated with lethal white foal syndrome in horses," *Mamm. Genome*, 1998, 9:306-309.

Sheffield et al., "Identification of Novel Rhodopsin Mutations Associated with Retinitis Pigmentosa by GC-clamped Denaturing Gradient Gel Electrophoresis," *Am. J. Hum. Genet.*, 1991, 49:699-706.

Sheffield et al., "Attachment of a 40-base-pair G+C-rich sequence (GC-clamp) to genomic DNA fragments by the polymerase chain reaction results in improved detection of single-base changes," *Proc. Natl. Acad. Sci. USA*, 1989, 86:232-236.

Shenk et al., "Biochemical Method for Mapping Mutational Alternations in DNA with S1 Nuclease: The Location of Deletions and Temperature-Sensitive Mutations in Simian Virus 40," *Proc. Natl. Acad. Sci. USA*, 1975, 72(3):989-993.

Shin et al., "A Kinase-Negative Mutation of DNA-$PK_{CS}$ in Equine SCID Results in Defective Coding and Signal Joint Formation," *J. Immunol.*, 1997, 158:3565-3569.

Smith and Waterman, "Comparison of Biosequences," *Adv. Appl. Math.*, 1981, 2:482-489.

Spirito et al., "Animal Models for Skin Blistering Conditions: Absence of Laminin 5 Causes Hereditary Junctional Mechanobullous Disease in the Belgian Horse," *J. Invest. Dermatol.*, 2002, 119:684-691.

Sponseller et al., "Muscular weakness and recumbency in a Quarter Horse colt due to glycogen branching enzyme deficiency," *Equine Vet. Educ.*, 2003, 15(4):182-188.

Thon et al., "Isolation of Human Glycogen Branching Enzyme cDNAs by Screening Complementation in Yeast," *J. Biol. Chem.*, 1993, 268(10):7509-7513.

Tijssen, "Overview of principles of hybridization and the strategy of nucleic acid probe assays," *Laboratory Techniques in Biochemistry and Molecular Biology. Hybridization with Nucleic Acid Probes*, 1993, part 1, Chapter 2, pp. 19-78.

Ulevitch, "Molecular Mechanisms of Innate Immunity," *Immunol. Res.*, 2000, 2 1/2-3:49-54.

Valberg et al., "Glycogen Branching Enzyme Deficiency in Quarter Horse Foals," *J. Vet. Intern. Med.*, 2001, 15:572-580.

Walker et al., "Strand displacement amplification-an isothermal *in vitro* DNA amplification technique," *Nucl. Acids. Res.*, 1992, 20(7):1691-1969.

Walker et al., "Isothermal *in vitro* amplification of DNA by a restriction enzyme/DNA polymerase system," *Proc. Natl. Acad. Sci. USA*, 1992, 89:392-396.

Ward et al., "Genetic mapping of GBE1 and its association with glycogen storage disease IV in American Quarter horses," *Cytogenet Genome Res.*, 2003, 102:201-206.

Wartell et al., "Detecting base pair substitutions in DNA fragments by temperature-gradient gel electrophoresis," *Nucl. Acids Res.*, 1990, 18(9):2699-2705.

Weiss, "Hot Prospect for New Gene Amplifier," *Science*, 1991, 254:1292-1293.

White et al., "Detecting Single Base Substitutions as Heteroduplex Polymorphisms," *Genomics*, 1992, 12:301-306.

Zimmerman and Gold, "Isolation and Characterization of Glycogen Branching Enzyme from Rabbit Liver," *Biochemistry*, 1983, 22:3387-3392.

Ausems et al., "Phenotypic expression of late-onset glycogen storage disease type II: identification of asymptomatic adults through family studies and review of reported families," *Neuromuscular Disorders*, 2000, 10:467-71.

Bandsma et al., "Disturbed lipid metabolism in glycogen storage disease type 1," *Eur. J. Pediatr.*, 2002, 161:S65-S69.

Burchell, "Glycogen storage diseases and the liver," *Baillière's Clinical Gastroenterology*, 1998, 12(2):337-354.

Chen et al., "Prenatal diagnosis in glycogen storage diseases," *Prenat. Diagn.*, 2002, 22:357-359.

Chen and Amalfitano, "Towards a molecular therapy for glycogen storage disease type II (Pompe disease)," *Molecular Medicine Today*, 2000, 6:245-251.

Chen et al., "Prenatal diagnosis in glycogen storage diseases," *Prenat. Diagn.*, 2001, 22:357-359.

Chou, "The Molecular Basis of Type 1 Glycogen Storage Diseases," *Current Molecular Medicine*, 2001, 1:25-44.

Chou, "Type 1 Glycogen Storage Diseases: Disorders of the Glucose-6-Posphatase Complex," *Current Molecular Medicine*, 2002, 2:121-143.

Chou et al., "Adenovirus-mediated gene therapy in a mouse model of glycogen storage disease type 1a," *Eur. J. Pediatr.*, 2002, 161:S56-S61.

DiMauro and Bruno, "Glycogen storage diseases of muscle," *Current Opinion in Neurology*, 1998, 11:477-484.

DiMauro et al., "Myophosphorylase Deficiency (Glycogenosis Type V; McArdle Disease)," *Current Molecular Medicine*, 2002, 2:189-196.

DiMauro and Lamperti, "Muscle Glycogenoses," *Muscle Nerve*, 2001, 24:984-999.

Fischer et al., "Acid maltase deficiency (glycogen storage disease type II [Pompe's disease]) as a differential diagnosis of anorexia nervosa," *Dtsch. Med. Wschr.*, 1999, 124:925-929, English abstract.

Garty et al., "Immune Deficiency in Glycogen Storage Disease Type 1B," *Isr. J. Med. Sci.*, 1996, 32:1276-1281.

Gollob et al., "Glycogen storage disease as a unifying mechanism of disease in the PRKAG2 cardiac syndrome," *Biochem. Soc. Trans.*, 2003, 31(1):228-231.

Gordon, "Glycogenosis type V or McArdle's disease," *Developmental Medicine & Child Neurology*, 2003, 45:640-644.

Hesselink et al., "Lysosomal dysfunction in muscle with special reference to glycogen storage disease type II," *Biochim. Biophys. Acta*, 2003, 1637:164-170.

Janecke et al., "Molecular Genetics of Type 1 Glycogen Storage Disease," *Molecular Genetics and Metabolism*, 2001, 73:117-125.

Kannourakis, "Glycogen Storage Disease," *Seminars in Hematology*, 2002, 39(2):103-106.

Karasawa et al., "A Case of Glycogen Storage Disease Type Ia With Multiple Hepatic Adenomas and G727T Mutation in the Glucose-6-Phosphatase Gene, and a Comparison With Other Mutations Previously Reported," *Am. J. Gastroenterol.*, 1998, 93:1550-1553.

Labrune et al., "Hepatocellular Adenomas in Glycogen Storage Disease Type I and III: A Series of 43 Patients and Review of the Literature," *J. Pediatr. Gastroenterol. Nutr.*, 1997, 24:276-279.

Labrune, "Glycogen storage disease type I: indications for liver and/or kidney transplantation," *Eur. J. Pediatr.*, 2002, 161:S53-S55.

Lee, "Glycogen storage disease type I: pathophysiology of liver adenomas," *Eur. J. Pediatr.*, 2002, 161:S46-S49.

Mairovitz et al., "Contraception and pregnancy in women affected by glycogen storage diseases," *Eur. J. Pediatr.*, 2002, 161:S97-S101.

Matern et al., "Liver transplantation for glycogen storage disease types I, III, and IV," *Eur. J. Pediatr.*, 1999, 158(Suppl. 2):S43-S48.

Moses and Parvari, "The Variable Presentations of Glycogen Storage Disease Type IV: A Review of Clinical, Enzymatic and Molecular Studies," *Current Molecular Medicine*, 2002, 2:177-188.

Moses, "Historical highlights and unsolved problems in glycogen storage disease type 1," *Eur. J. Pediatr.*, 2002, 161:S2-S9.

Poenaru, "Approach to Gene Therapy of Glycogenosis Type II (Pompe Disease)," *Molecular Genetics and Metabolism*, 2000, 70:163-169.

Raben et al., "Acid α-Glucosidase Deficiency (Glycogenosis Type II, Pompe Disease)," *Current Molecular Medicine*, 2002, 2:145-166.

Rake et al., "Guidelines for management of glycogen storage disease type I—European Study on Glycogen Storage Disease Type I (ESGSD I)," *Eur. J. Pediatr.*, 2002, 161:S112-S119.

Rake et al., "Glycogen storage disease type Ia: recent experience with mutation analysis, a summary of mutations reported in the literature and a newly developed diagnostic flowchart," *Eur. J. Pediatr.*, 2000, 159:322-330.

Schönau et al., "The muscle-bone relationship: methods and management—perspectives in glycogen storage disease," *Eur. J. Pediatr.*, 2002, 161:S50-S52.

Shen and Chen, "Molecular Characterization of Glycogen Storage Disease Type III," *Current Molecular Medicine*, 2002, 2:167-175.

Triomphe, "Glycogen Storage Disease: A Basic Understanding and Guide to Nursing Care," *Journal of Pediatric Nursing*, 1997, 12(4):238-249.

Veiga-da-Cunha et al., "How many forms of glycogen storage disease type I?" *Eur. J. Pediatr.*, 2000, 159:314-318.

Visser et al., "Consensus guidelines for management of glycogen storage disease type 1b—European Study of Glycogen Storage Disease Type 1," *Eur. J. Pediatr.*, 2002, 161:S120-S123.

Wolfsdorf et al., "Glycogen Storage Diseases," *Pediatric Endocrinology*, 1999, 28(4):801-823.

\* cited by examiner

Figure 1A. Alignment of the full-length horse and human GBE1 amino acid sequences.

```
             1                                                           50
HORSE    MAAP...AAR ADGSDAALAA ALADVPDLGR LLEVDPYLKP YAPDFQRRYN
HUMAN    MAAPMTPAAR PEDYEAALNA ALADVPELAR LLEIDPYLKP YAVDFQRRYK 51                                                          100
HORSE    RFSQTLDNIG KNEGGIDKFS RGYESFGVHR CADGGLYCKE WAPGAEGVFL
HUMAN    QFSQILKNIG ENEGGIDKFS RGYESFGVHR CADGGLYSKE WAPGAEGVFL 101                                                         150
HORSE    TGDFNDWNPF SYPYKKLDYG KWDLYIPPKP NKSLLVPHGS KLKVVIRSKS
HUMAN    TGDFNGWNPF SYPYKKLDYG KWELYIPPKQ NKSVLVPHGS KLKVVITSKS 151                                                         200
HORSE    GEILYRISPW AKYVVRESGN VNYDWIHWDP EQPYKFKHSR PKKPRSLRIY
HUMAN    GEILYRISPW AKYVVREGDN VNYDWIHWDP EHSYEFKHSR PKKPRSLRIY 201                                                         250
HORSE    ESHVGISSHE GKIASYKHFT CNVLPRIKGL GYNCIQMMAI MEHAYYASFG
HUMAN    ESHVGISSHE GKVASYKHFT CNVLPRIKGL GYNCIQLMAI MEHAYYASFG 251                                                         300
HORSE    YQITSFFAAS SRYGTPEELK ELVDTAHSMG ITVLLDVVHS HASKNSEDGL
HUMAN    YQITSFFAAS SRYGTPEELQ ELVDTAHSMG IIVLLDVVHS HASKNSADGL 301                                                         350
HORSE    NMFDGTDSCY FHSGPRGTHD LWDSRLFIYS SWEVLRFLLS NIRWWLEEYG
HUMAN    NMFDGTDSCY FHSGPRGTHD LWDSRLFAYS SWEVLRFLLS NIRWWLEEYR 351                                                         400
HORSE    FDGFRFDGVT SMLYHHHGIG ASFSGDYHEY FGLQVDEDAL TYLMLANHLV
HUMAN    FDGFRFDGVT SMLYHHHGVG QGFSGDYSEY FGLQVDEDAL TYLMLANHLV 401                                                         450
HORSE    HTLYPDSITI AEDVSGMPAL CSPISQGGGG FDYRLAMAIP DKWIQLVKEF
HUMAN    HTLCPDSITI AEDVSGMPAL CSPISQGGGG FDYRLAMAIP DKWIQLLKEF 451                                                         500
HORSE    KDEDWNMGNI VYTLTNRRHL EKCIAYAESH DQALVGDKSL AFWLMDAEMY
HUMAN    KDEDWNMGDI VYTLTNRRYL EKCIAYAESH DQALVGDKSL AFWLMDAEMY 501                                                         550
HORSE    TNMSVLTPFT PVIDRGIQLH KMIRLITHAL GGEGYLNFMG NEFGHPEWLD
HUMAN    TNMSVLTPFT PVIDRGIQLH KMIRLITHGL GGEGYLNFMG NEFGHPEWLD 551                                                         600
HORSE    FPRKGNNESY HYARRQFHLT DDDLLRYKFL NNFDRDMNKL EERCGWLSAP
HUMAN    FPRKGNNESY HYARRQFHLT DDDLLRYKFL NNFDRDMNRL EERYGWLAAP 601                                                         650
HORSE    QAFVSEKHEG NKVIAFERAA LLFIFNFHPS KSYTNYRVGT TLPGKFKIVL
```

```
HUMAN    QAYVSEKHEG  NKIIAFERAG  LLFIFNFHPS  KSYTDYRVGT  ALPGKFKIVL 651                                                    700
HORSE    DSDAAEYGGH  QRLDHNTDFF  SEPYEHNERP  SSLLVYIPSR  VALILQNVDP
HUMAN    DSDAAEYGGH  QRLDHSTDFF  SEAFEHNGRP  YSLLVYIPSR  VALILQNVDL

701
HORSE    PN*
HUMAN    PN*
```

Figure 1B. GBE1 exon 1 amino acid sequence alignment in available mammalian species.

```
         1                                                      48
HORSE    MAA...PAAR  ADGSDAALAA  ALADVPDLGR  LLEVDPYLKP  YAPDFQRR~
CAT      MAA...PVAR  GECSEAALAA  ALADVPELAR  LLELDPYLKP  FALDFQRR~
HUMAN    MAAPMTPAAR  PEDYEAALNA  ALADVPELAR  LLEIDPYLKP  YAVDFQRR~
MOUSE    MAAPAAPAAG  ETGPDARLEA  ALADVPELAR  LLEIDPYLKP  FAADFQRR~
RAT      MAAPAAPAAE  EKGSEAQLKA  ALADVPELGR  LLEIDPYLKP  YAADFQRR~
PIG      MAASAGAPAP  AEGSEEALAS  ALADVPELAR  LLETDPYLKP  YAPDFQRR~
```

Figure 2. Equine GBE1 5' end and cDNA sequence used for mutation analysis.

```
-309                                                              GGGCTGCCG

-300   CCGCGGGAGG  CGCCGCAAGC  GGACGAGCGG  AGGGGCGCCG  GCCGGCTCGG

-250   GGAGGGCAGG  CGGCCGCGCC  GGGAGGGGGG  CGGCCGGGCC  CAGGTGCGCG

-200   CGGCGGGCGG  GCGCCGCCTC  CTCCGCCGGC  CGCTCCTCCC  CGCCGCGGGG

-150   GCAGGGCAGC  GCCGCGCTCG  CCGCTATAAA  GGGCCCCGGG  CCGCAGCCGC

-100   TCGCCTCGGC  GTCCTCGGCT  CCGCCCTCGC  GCCGGCCACT  CCGCGGAGCT

-50   CGTTCCCGCT  CGAGCGGCTC  GGGCCTCGGC  TACTCGGGCT  GCGGCCGAAG

1   ATGGCGGCGC  CGGCGGCTCG  GGCCGACGGC  TCCGACGCGG  CGCTGGCGGC

51   GGCCCTGGCG  GACGTGCCCG  ACCTGGGCCG  CCTTCTGGAG  GTCGACCCGT
              !                                   <  >
 101   ACCTGAAGCC  CTACGCCCCG  GACTTCCAGC  GCAGGTATAA  CCGGTTTAGC
```

Figure 3. Sequence chromatograms of nucleotides 92-108 in a PCR product from the genomic DNA of a control (5A), a carrier (5B) and an affected (5C) horse.
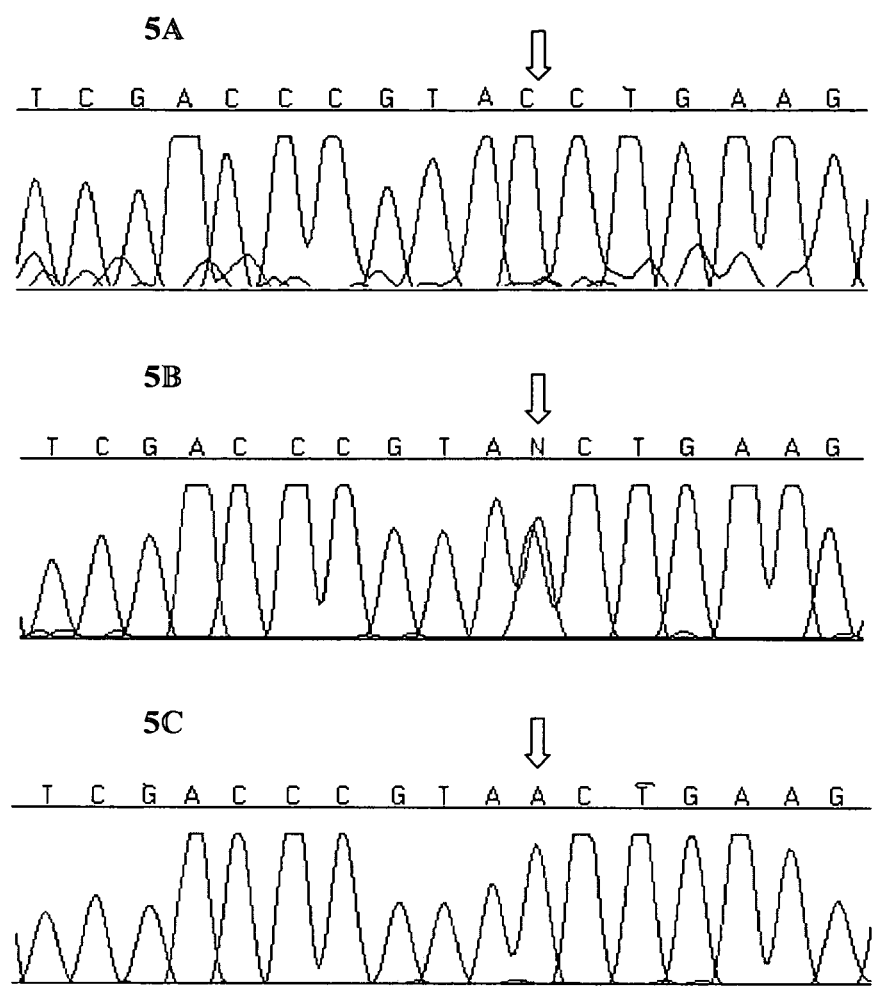

SEQUENCE LISTING

```
<160> NUMBER OF SEQ ID NOS: 31

<210> SEQ ID NO 1
<211> LENGTH: 699
<212> TYPE: PRT
<213> ORGANISM: Equus caballus

<400> SEQUENCE: 1

Met Ala Ala Pro Ala Ala Arg Ala Asp Gly Ser Asp Ala Ala Leu Ala
1               5                   10                  15

Ala Ala Leu Ala Asp Val Pro Asp Leu Gly Arg Leu Leu Glu Val Asp
            20                  25                  30

Pro Tyr Leu Lys Pro Tyr Ala Pro Asp Phe Gln Arg Arg Tyr Asn Arg
        35                  40                  45

Phe Ser Gln Thr Leu Asp Asn Ile Gly Lys Asn Glu Gly Gly Ile Asp
    50                  55                  60

Lys Phe Ser Arg Gly Tyr Glu Ser Phe Gly Val His Arg Cys Ala Asp
65                  70                  75                  80

Gly Gly Leu Tyr Cys Lys Glu Trp Ala Pro Gly Ala Glu Gly Val Phe
                85                  90                  95

Leu Thr Gly Asp Phe Asn Asp Trp Asn Pro Phe Ser Tyr Pro Tyr Lys
            100                 105                 110
```

-continued

```
Lys Leu Asp Tyr Gly Lys Trp Asp Leu Tyr Ile Pro Pro Lys Pro Asn
        115                 120                 125
Lys Ser Leu Leu Val Pro His Gly Ser Lys Leu Lys Val Val Ile Arg
        130                 135                 140
Ser Lys Ser Gly Glu Ile Leu Tyr Arg Ile Ser Pro Trp Ala Lys Tyr
145                 150                 155                 160
Val Val Arg Glu Ser Gly Asn Val Asn Tyr Asp Trp Ile His Trp Asp
                165                 170                 175
Pro Glu Gln Pro Tyr Lys Phe Lys His Ser Arg Pro Lys Lys Pro Arg
            180                 185                 190
Ser Leu Arg Ile Tyr Glu Ser His Val Gly Ile Ser Ser His Glu Gly
        195                 200                 205
Lys Ile Ala Ser Tyr Lys His Phe Thr Cys Asn Val Leu Pro Arg Ile
        210                 215                 220
Lys Gly Leu Gly Tyr Asn Cys Ile Gln Met Met Ala Ile Met Glu His
225                 230                 235                 240
Ala Tyr Tyr Ala Ser Phe Gly Tyr Gln Ile Thr Ser Phe Phe Ala Ala
                245                 250                 255
Ser Ser Arg Tyr Gly Thr Pro Glu Glu Leu Lys Glu Leu Val Asp Thr
            260                 265                 270
Ala His Ser Met Gly Ile Thr Val Leu Leu Asp Val Val His Ser His
        275                 280                 285
Ala Ser Lys Asn Ser Glu Asp Gly Leu Asn Met Phe Asp Gly Thr Asp
        290                 295                 300
Ser Cys Tyr Phe His Ser Gly Pro Arg Gly Thr His Asp Leu Trp Asp
305                 310                 315                 320
Ser Arg Leu Phe Ile Tyr Ser Ser Trp Glu Val Leu Arg Phe Leu Leu
                325                 330                 335
Ser Asn Ile Arg Trp Trp Leu Glu Glu Tyr Gly Phe Asp Gly Phe Arg
            340                 345                 350
Phe Asp Gly Val Thr Ser Met Leu Tyr His His His Gly Ile Gly Ala
        355                 360                 365
Ser Phe Ser Gly Asp Tyr His Glu Tyr Phe Gly Leu Gln Val Asp Glu
        370                 375                 380
Asp Ala Leu Thr Tyr Leu Met Leu Ala Asn His Leu Val His Thr Leu
385                 390                 395                 400
Tyr Pro Asp Ser Ile Thr Ile Ala Glu Asp Val Ser Gly Met Pro Ala
                405                 410                 415
Leu Cys Ser Pro Ile Ser Gln Gly Gly Gly Phe Asp Tyr Arg Leu
            420                 425                 430
Ala Met Ala Ile Pro Asp Lys Trp Ile Gln Leu Val Lys Glu Phe Lys
        435                 440                 445
Asp Glu Asp Trp Asn Met Gly Asn Ile Val Tyr Thr Leu Thr Asn Arg
        450                 455                 460
Arg His Leu Glu Lys Cys Ile Ala Tyr Ala Glu Ser His Asp Gln Ala
465                 470                 475                 480
Leu Val Gly Asp Lys Ser Leu Ala Phe Trp Leu Met Asp Ala Glu Met
                485                 490                 495
Tyr Thr Asn Met Ser Val Leu Thr Pro Phe Thr Pro Val Ile Asp Arg
            500                 505                 510
Gly Ile Gln Leu His Lys Met Ile Arg Leu Ile Thr His Ala Leu Gly
        515                 520                 525
```

```
Gly Glu Gly Tyr Leu Asn Phe Met Gly Asn Glu Phe Gly His Pro Glu
        530                 535                 540

Trp Leu Asp Phe Pro Arg Lys Gly Asn Asn Glu Ser Tyr His Tyr Ala
545                 550                 555                 560

Arg Arg Gln Phe His Leu Thr Asp Asp Leu Leu Arg Tyr Lys Phe
                565                 570                 575

Leu Asn Asn Phe Asp Arg Asp Met Asn Lys Leu Glu Glu Arg Cys Gly
                580                 585                 590

Trp Leu Ser Ala Pro Gln Ala Phe Val Ser Glu Lys His Glu Gly Asn
        595                 600                 605

Lys Val Ile Ala Phe Glu Arg Ala Ala Leu Leu Phe Ile Phe Asn Phe
        610                 615                 620

His Pro Ser Lys Ser Tyr Thr Asn Tyr Arg Val Gly Thr Thr Leu Pro
625                 630                 635                 640

Gly Lys Phe Lys Ile Val Leu Asp Ser Asp Ala Ala Glu Tyr Gly Gly
                645                 650                 655

His Gln Arg Leu Asp His Asn Thr Asp Phe Phe Ser Glu Pro Tyr Glu
                660                 665                 670

His Asn Glu Arg Pro Ser Ser Leu Leu Val Tyr Ile Pro Ser Arg Val
        675                 680                 685

Ala Leu Ile Leu Gln Asn Val Asp Pro Pro Asn
        690                 695

<210> SEQ ID NO 2
<211> LENGTH: 702
<212> TYPE: PRT
<213> ORGANISM: Homo sapiens

<400> SEQUENCE: 2

Met Ala Ala Pro Met Thr Pro Ala Ala Arg Pro Glu Asp Tyr Glu Ala
1               5                   10                  15

Ala Leu Asn Ala Ala Leu Ala Asp Val Pro Glu Leu Ala Arg Leu Leu
            20                  25                  30

Glu Ile Asp Pro Tyr Leu Lys Pro Tyr Ala Val Asp Phe Gln Arg Arg
        35                  40                  45

Tyr Lys Gln Phe Ser Gln Ile Leu Lys Asn Ile Gly Glu Asn Glu Gly
    50                  55                  60

Gly Ile Asp Lys Phe Ser Arg Gly Tyr Glu Ser Phe Gly Val His Arg
65                  70                  75                  80

Cys Ala Asp Gly Gly Leu Tyr Ser Lys Glu Trp Ala Pro Gly Ala Glu
                85                  90                  95

Gly Val Phe Leu Thr Gly Asp Phe Asn Gly Trp Asn Pro Phe Ser Tyr
            100                 105                 110

Pro Tyr Lys Lys Leu Asp Tyr Gly Lys Trp Glu Leu Tyr Ile Pro Pro
        115                 120                 125

Lys Gln Asn Lys Ser Val Leu Val Pro His Gly Ser Lys Leu Lys Val
    130                 135                 140

Val Ile Thr Ser Lys Ser Gly Glu Ile Leu Tyr Arg Ile Ser Pro Trp
145                 150                 155                 160

Ala Lys Tyr Val Val Arg Glu Gly Asp Asn Val Asn Tyr Asp Trp Ile
                165                 170                 175

His Trp Asp Pro Glu His Ser Tyr Glu Phe Lys His Ser Arg Pro Lys
            180                 185                 190

Lys Pro Arg Ser Leu Arg Ile Tyr Glu Ser His Val Gly Ile Ser Ser
        195                 200                 205
```

-continued

His Glu Gly Lys Val Ala Ser Tyr Lys His Phe Thr Cys Asn Val Leu
    210                 215                 220

Pro Arg Ile Lys Gly Leu Gly Tyr Asn Cys Ile Gln Leu Met Ala Ile
225                 230                 235                 240

Met Glu His Ala Tyr Ala Ser Phe Gly Tyr Gln Ile Thr Ser Phe
                245                 250                 255

Phe Ala Ala Ser Ser Arg Tyr Gly Thr Pro Glu Glu Leu Gln Glu Leu
            260                 265                 270

Val Asp Thr Ala His Ser Met Gly Ile Ile Val Leu Leu Asp Val Val
        275                 280                 285

His Ser His Ala Ser Lys Asn Ser Ala Asp Gly Leu Asn Met Phe Asp
    290                 295                 300

Gly Thr Asp Ser Cys Tyr Phe His Ser Gly Pro Arg Gly Thr His Asp
305                 310                 315                 320

Leu Trp Asp Ser Arg Leu Phe Ala Tyr Ser Ser Trp Glu Val Leu Arg
                325                 330                 335

Phe Leu Leu Ser Asn Ile Arg Trp Trp Leu Glu Glu Tyr Arg Phe Asp
            340                 345                 350

Gly Phe Arg Phe Asp Gly Val Thr Ser Met Leu Tyr His His His Gly
        355                 360                 365

Val Gly Gln Gly Phe Ser Gly Asp Tyr Ser Glu Tyr Phe Gly Leu Gln
    370                 375                 380

Val Asp Glu Asp Ala Leu Thr Tyr Leu Met Leu Ala Asn His Leu Val
385                 390                 395                 400

His Thr Leu Cys Pro Asp Ser Ile Thr Ile Ala Glu Asp Val Ser Gly
                405                 410                 415

Met Pro Ala Leu Cys Ser Pro Ile Ser Gln Gly Gly Gly Phe Asp
            420                 425                 430

Tyr Arg Leu Ala Met Ala Ile Pro Asp Lys Trp Ile Gln Leu Leu Lys
        435                 440                 445

Glu Phe Lys Asp Glu Asp Trp Asn Met Gly Asp Ile Val Tyr Thr Leu
    450                 455                 460

Thr Asn Arg Arg Tyr Leu Glu Lys Cys Ile Ala Tyr Ala Glu Ser His
465                 470                 475                 480

Asp Gln Ala Leu Val Gly Asp Lys Ser Leu Ala Phe Trp Leu Met Asp
                485                 490                 495

Ala Glu Met Tyr Thr Asn Met Ser Val Leu Thr Pro Phe Thr Pro Val
            500                 505                 510

Ile Asp Arg Gly Ile Gln Leu His Lys Met Ile Arg Leu Ile Thr His
        515                 520                 525

Gly Leu Gly Gly Glu Gly Tyr Leu Asn Phe Met Gly Asn Glu Phe Gly
    530                 535                 540

His Pro Glu Trp Leu Asp Phe Pro Arg Lys Gly Asn Asn Glu Ser Tyr
545                 550                 555                 560

His Tyr Ala Arg Arg Gln Phe His Leu Thr Asp Asp Asp Leu Leu Arg
                565                 570                 575

Tyr Lys Phe Leu Asn Asn Phe Asp Arg Asp Met Asn Arg Leu Glu Glu
            580                 585                 590

Arg Tyr Gly Trp Leu Ala Ala Pro Gln Ala Tyr Val Ser Glu Lys His
        595                 600                 605

Glu Gly Asn Lys Ile Ile Ala Phe Glu Arg Ala Gly Leu Leu Phe Ile
    610                 615                 620

-continued

```
Phe Asn Phe His Pro Ser Lys Ser Tyr Thr Asp Tyr Arg Val Gly Thr
625                 630                 635                 640

Ala Leu Pro Gly Lys Phe Lys Ile Val Leu Asp Ser Asp Ala Ala Glu
            645                 650                 655

Tyr Gly Gly His Gln Arg Leu Asp His Ser Thr Asp Phe Phe Ser Glu
            660                 665                 670

Ala Phe Glu His Asn Gly Arg Pro Tyr Ser Leu Leu Val Tyr Ile Pro
            675                 680                 685

Ser Arg Val Ala Leu Ile Leu Gln Asn Val Asp Leu Pro Asn
            690                 695                 700

<210> SEQ ID NO 3
<211> LENGTH: 45
<212> TYPE: PRT
<213> ORGANISM: Equus caballus

<400> SEQUENCE: 3

Met Ala Ala Pro Ala Ala Arg Ala Asp Gly Ser Asp Ala Ala Leu Ala
1               5                   10                  15

Ala Ala Leu Ala Asp Val Pro Asp Leu Gly Arg Leu Leu Glu Val Asp
            20                  25                  30

Pro Tyr Leu Lys Pro Tyr Ala Pro Asp Phe Gln Arg Arg
        35                  40                  45

<210> SEQ ID NO 4
<211> LENGTH: 45
<212> TYPE: PRT
<213> ORGANISM: Felis cattus

<400> SEQUENCE: 4

Met Ala Ala Pro Val Ala Arg Gly Glu Cys Ser Glu Ala Ala Leu Ala
1               5                   10                  15

Ala Ala Leu Ala Asp Val Pro Glu Leu Ala Arg Leu Leu Glu Leu Asp
            20                  25                  30

Pro Tyr Leu Lys Pro Phe Ala Leu Asp Phe Gln Arg Arg
        35                  40                  45

<210> SEQ ID NO 5
<211> LENGTH: 48
<212> TYPE: PRT
<213> ORGANISM: Homo sapiens

<400> SEQUENCE: 5

Met Ala Ala Pro Met Thr Pro Ala Ala Arg Pro Glu Asp Tyr Glu Ala
1               5                   10                  15

Ala Leu Asn Ala Ala Leu Ala Asp Val Pro Glu Leu Ala Arg Leu Leu
            20                  25                  30

Glu Ile Asp Pro Tyr Leu Lys Pro Tyr Ala Val Asp Phe Gln Arg Arg
        35                  40                  45

<210> SEQ ID NO 6
<211> LENGTH: 48
<212> TYPE: PRT
<213> ORGANISM: Mus musculus

<400> SEQUENCE: 6

Met Ala Ala Pro Ala Ala Pro Ala Ala Gly Glu Thr Gly Pro Asp Ala
1               5                   10                  15

Arg Leu Glu Ala Ala Leu Ala Asp Val Pro Glu Leu Ala Arg Leu Leu
            20                  25                  30
```

```
Glu Ile Asp Pro Tyr Leu Lys Pro Phe Ala Ala Asp Phe Gln Arg Arg
            35                  40                  45

<210> SEQ ID NO 7
<211> LENGTH: 48
<212> TYPE: PRT
<213> ORGANISM: Rattus norvegicus

<400> SEQUENCE: 7

Met Ala Ala Pro Ala Ala Pro Ala Ala Glu Glu Lys Gly Ser Glu Ala
  1               5                  10                  15

Gln Leu Lys Ala Ala Leu Ala Asp Val Pro Glu Leu Gly Arg Leu Leu
                20                  25                  30

Glu Ile Asp Pro Tyr Leu Lys Pro Tyr Ala Ala Asp Phe Gln Arg Arg
            35                  40                  45

<210> SEQ ID NO 8
<211> LENGTH: 48
<212> TYPE: PRT
<213> ORGANISM: Sus scrofa

<400> SEQUENCE: 8

Met Ala Ala Ser Ala Gly Ala Pro Ala Pro Ala Glu Gly Ser Glu Glu
  1               5                  10                  15

Ala Leu Ala Ser Ala Leu Ala Asp Val Pro Glu Leu Ala Arg Leu Leu
                20                  25                  30

Glu Thr Asp Pro Tyr Leu Lys Pro Tyr Ala Pro Asp Phe Gln Arg Arg
            35                  40                  45

<210> SEQ ID NO 9
<211> LENGTH: 459
<212> TYPE: DNA
<213> ORGANISM: Equus caballus

<400> SEQUENCE: 9
gggctgccgc cgcgggaggc gccgcaagcg gacgagcgga ggggcgccgg ccggctcggg     60
gagggcaggc ggccgcgccg ggaggggggc ggccgggccc aggtgcgcgc ggcgggcggg    120
cgccgcctcc tccgccggcc gctcctcccc gccgcggggg cagggcagcg ccgcgctcgc    180
cgctataaag ggccccgggc cgcagccgct cgcctcggcg tcctcggctc cgccctcgcg    240
ccggccactc cgcggagctc gttcccgctc gagcggctcg ggcctcggct actcgggctg    300
cggccgaaga tggcggcgcc ggcggctcgg gccgacggct ccgacgcggc gctggcggcg    360
gccctggcgg acgtgcccga cctgggccgc cttctggagg tcgacccgta cctgaagccc    420
tacgccccgg acttccagcg caggtataac cggtttagc                            459

<210> SEQ ID NO 10
<211> LENGTH: 17
<212> TYPE: DNA
<213> ORGANISM: Equus caballus

<400> SEQUENCE: 10
tcgacccgta cctgaag                                                    17

<210> SEQ ID NO 11
<211> LENGTH: 17
<212> TYPE: DNA
<213> ORGANISM: Equus caballus
<220> FEATURE:
<221> NAME/KEY: misc_feature
```

```
<222> LOCATION: 11
<223> OTHER INFORMATION: N = A, T, C or G

<400> SEQUENCE: 11
tcgacccgta nctgaag                                                17

<210> SEQ ID NO 12
<211> LENGTH: 17
<212> TYPE: DNA
<213> ORGANISM: Equus caballus

<400> SEQUENCE: 12
tcgacccgta actgaag                                                17

<210> SEQ ID NO 13
<211> LENGTH: 18
<212> TYPE: DNA
<213> ORGANISM: Equus caballus

<400> SEQUENCE: 13
gaatccattt tcgtaccc                                               18

<210> SEQ ID NO 14
<211> LENGTH: 19
<212> TYPE: DNA
<213> ORGANISM: Equus caballus

<400> SEQUENCE: 14
accaggagtc tgtcccatc                                              19

<210> SEQ ID NO 15
<211> LENGTH: 19
<212> TYPE: DNA
<213> ORGANISM: Equus caballus

<400> SEQUENCE: 15
cctgaagagc taaaagaat                                              19

<210> SEQ ID NO 16
<211> LENGTH: 19
<212> TYPE: DNA
<213> ORGANISM: Equus caballus

<400> SEQUENCE: 16
ccacgatcaa taactggag                                              19

<210> SEQ ID NO 17
<211> LENGTH: 18
<212> TYPE: DNA
<213> ORGANISM: Equus caballus

<400> SEQUENCE: 17
gaagattgga acatgggc                                               18

<210> SEQ ID NO 18
<211> LENGTH: 20
<212> TYPE: DNA
<213> ORGANISM: Equus caballus

<400> SEQUENCE: 18
gatccacgtt ctgaagaatg                                             20

<210> SEQ ID NO 19
```

```
<211> LENGTH: 18
<212> TYPE: DNA
<213> ORGANISM: Equus caballus

<400> SEQUENCE: 19
gagatcgccc ccactcac                                                   18

<210> SEQ ID NO 20
<211> LENGTH: 20
<212> TYPE: DNA
<213> ORGANISM: Equus caballus

<400> SEQUENCE: 20
ctgtcaggcg cttcagactc                                                 20

<210> SEQ ID NO 21
<211> LENGTH: 21
<212> TYPE: DNA
<213> ORGANISM: Equus caballus

<400> SEQUENCE: 21
tttagccaga ctttggacaa c                                               21

<210> SEQ ID NO 22
<211> LENGTH: 20
<212> TYPE: DNA
<213> ORGANISM: Equus caballus

<400> SEQUENCE: 22
ctctttgcag tataagcccc                                                 20

<210> SEQ ID NO 23
<211> LENGTH: 20
<212> TYPE: DNA
<213> ORGANISM: Equus caballus

<400> SEQUENCE: 23
aaattgtgct agattcggac                                                 20

<210> SEQ ID NO 24
<211> LENGTH: 21
<212> TYPE: DNA
<213> ORGANISM: Equus caballus

<400> SEQUENCE: 24
caaaagagaa gagggacgct c                                               21

<210> SEQ ID NO 25
<211> LENGTH: 20
<212> TYPE: DNA
<213> ORGANISM: Equus caballus

<400> SEQUENCE: 25
aaattgtgct agattcggac                                                 20

<210> SEQ ID NO 26
<211> LENGTH: 18
<212> TYPE: DNA
<213> ORGANISM: Equus caballus

<400> SEQUENCE: 26
tgcgctggaa gtccgggg                                                   18
```

<210> SEQ ID NO 27
<211> LENGTH: 2100
<212> TYPE: DNA
<213> ORGANISM: Equus caballus

<400> SEQUENCE: 27

| | | | | | | |
|---|---|---|---|---|---|---|
| atggcggcgc | cggcggctcg | ggccgacggc | tccgacgcgg | cgctggcggc | ggccctggcg | 60 |
| gacgtgcccg | acctgggccg | ccttctggag | gtcgacccgt | acctgaagcc | ctacgccccg | 120 |
| gacttccagc | gcaggtataa | ccggtttagc | cagactttgg | acaacattgg | aaagaatgaa | 180 |
| ggtggtattg | acaagttttc | cagaggttat | gaatcatttg | gcgtccacag | atgtgctgac | 240 |
| gggggcttat | actgcaaaga | gtgggccccg | ggagcagaag | gagtttttct | tactggagac | 300 |
| ttcaatgatt | ggaatccatt | ttcgtaccca | tacaaaaaac | tggattatgg | aaaatgggat | 360 |
| ctgtatatcc | caccaaagcc | taataaatcc | ctcctggtac | cgcatggatc | caaattaaag | 420 |
| gtagttatta | ggagtaaaag | tggagagatc | ttgtatcgta | tttcaccgtg | gcgaagtat | 480 |
| gtggttcgtg | aaagtggtaa | tgtgaattat | gattggatac | actgggatcc | agaacagcca | 540 |
| tataaattta | gcattccag | accaaagaag | ccaagaagtc | taagaattta | tgaatctcat | 600 |
| gtgggaattt | cttcccatga | aggaaaaata | gcttcttata | acattttac | atgcaacgta | 660 |
| ctaccaagaa | tcaaaggcct | tggatacaac | tgcattcaga | tgatggcaat | catggagcac | 720 |
| gcttactacg | ccagttttgg | ttaccagatc | acaagcttct | ttgcagcgtc | aagccgttac | 780 |
| ggaacacctg | aagagctaaa | agaattggtt | gacaccgctc | actcaatggg | tattacagtc | 840 |
| ctcttagatg | tagtgcacag | ccatgcctcc | aaaaattcag | aagatggatt | gaatatgttt | 900 |
| gatgggacag | actcctgtta | ttttcattct | ggacctagag | ggactcatga | tctttgggat | 960 |
| agtcgattgt | ttatctactc | cagctgggaa | gttttaagat | tccttctgtc | aaacataaga | 1020 |
| tggtggttgg | aagaatatgg | ctttgatggg | tttcgtttg | atggtgttac | atccatgctc | 1080 |
| tatcatcacc | atgaattgg | tgcaagcttt | tcaggtgatt | accatgaata | ttttggactc | 1140 |
| caagtagatg | aagacgcctt | gacttatctc | atgctggcca | atcatttggt | tcacacgttg | 1200 |
| tatccggatt | ctatcacaat | agctgaggat | gtctcaggaa | tgccggctct | gtgttctccg | 1260 |
| atttcccagg | gagggggtgg | ctttgactat | agattagcca | tggcaattcc | ggacaaatgg | 1320 |
| atccagctag | ttaaggagtt | taagatgaa | gattggaaca | tgggcaacat | agtgtacact | 1380 |
| ctcacaaaca | gacgccacct | tgaaaagtgc | atcgcttatg | cagagagcca | tgatcaggca | 1440 |
| ctcgttgggg | ataagtcact | ggcattttgg | ttgatggacg | ccgaaatgta | taccaacatg | 1500 |
| agtgttctga | cccctttac | tccagttatt | gatcgtggaa | tacagcttca | caaatgatt | 1560 |
| cgactcatta | ctcacgcact | cggtggagag | ggctatctca | atttcatggg | taatgaattt | 1620 |
| gggcatccgg | aatggctaga | cttcccaaga | aagggaata | atgagagcta | ccattatgcc | 1680 |
| agaaggcagt | tcatttaac | tgatgatgac | cttcttcgct | acaagttcct | aaataacttt | 1740 |
| gacagggata | tgaataaatt | ggaagaaaga | tgtggttggc | tttccgctcc | ccaggcattt | 1800 |
| gtgagtgaaa | agcatgaagg | caataaggtc | atcgcttttg | agagagcagc | tcttcttttt | 1860 |
| attttcaact | tccatccaag | caagagctac | accaattaca | gagtcggaac | gacattgcca | 1920 |
| gggaaattca | aaattgtgct | agattccgac | gcagcggaat | atggaggaca | ccagagattg | 1980 |
| gaccacaata | ccgatttctt | ttctgagcct | tatgagcata | atgagcgtcc | ctcttcyctt | 2040 |
| ttggtgtaca | ttccaagccg | agtggccctc | attcttcaga | acgtggatcc | gcccaactga | 2100 |

<210> SEQ ID NO 28

<211> LENGTH: 2100
<212> TYPE: DNA
<213> ORGANISM: Equus caballus

<400> SEQUENCE: 28

| | | | | | |
|---|---|---|---|---|---|
| atggcggcgc | cggcggctcg | ggccgacggc | tccgacgcgg | cgctggcggc | ggccctggcg | 60 |
| gacgtgcccg | acctgggccg | ccttctggag | gtcgacccgt | aactgaagcc | ctacgccccg | 120 |
| gacttccagc | gcaggtataa | ccggtttagc | cagactttgg | acaacattgg | aaagaatgaa | 180 |
| ggtggtattg | acaagttttc | cagaggttat | gaatcatttg | gcgtccacag | atgtgctgac | 240 |
| gggggcttat | actgcaaaga | gtgggccccg | ggagcagaag | gagttttctc | tactggagac | 300 |
| ttcaatgatt | ggaatccatt | ttcgtaccca | tacaaaaaac | tggattatgg | aaaatgggat | 360 |
| ctgtatatcc | caccaaagcc | taataaatcc | ctcctggtac | cgcatggatc | caaattaaag | 420 |
| gtagttatta | ggagtaaaag | tggagagatc | ttgtatcgta | tttcaccgtg | gcgaagtat | 480 |
| gtggttcgtg | aaagtggtaa | tgtgaattat | gattggatac | actgggatcc | agaacagcca | 540 |
| tataaattta | agcattccag | accaagaag | ccaagaagtc | taagaattta | tgaatctcat | 600 |
| gtgggaattt | cttcccatga | aggaaaaata | gcttcttata | acatttttac | atgcaacgta | 660 |
| ctaccaagaa | tcaaaggcct | tggatacaac | tgcattcaga | tgatggcaat | catggagcac | 720 |
| gcttactacg | ccagttttgg | ttaccagatc | acaagcttct | ttgcagcgtc | aagccgttac | 780 |
| ggaacacctg | aagagctaaa | agaattggtt | gacaccgctc | actcaatggg | tattacagtc | 840 |
| ctcttagatg | tagtgcacag | ccatgcctcc | aaaaattcag | aagatggatt | gaatatgttt | 900 |
| gatgggacag | actcctgtta | ttttcattct | ggacctagag | ggactcatga | tctttgggat | 960 |
| agtcgattgt | ttatctactc | cagctgggaa | gttttaagat | tccttctgtc | aaacataaga | 1020 |
| tggtggttgg | aagaatatgg | ctttgatggg | tttcgttttg | atggtgttac | atccatgctc | 1080 |
| tatcatcacc | atggaattgg | tgcaagcttt | tcaggtgatt | accatgaata | ttttggactc | 1140 |
| caagtagatg | aagacgcctt | gacttatctc | atgctggcca | atcatttggt | tcacacgttg | 1200 |
| tatccggatt | ctatcacaat | agctgaggat | gtctcaggaa | tgccggctct | gtgttctccg | 1260 |
| atttcccagg | gaggggtgg | ctttgactat | agattagcca | tggcaattcc | ggacaaatgg | 1320 |
| atccagctag | ttaaggagtt | taagatgaa | gattggaaca | tgggcaacat | agtgtacact | 1380 |
| ctcacaaaca | gacgccacct | tgaaaagtgc | atcgcttatg | cagagagcca | tgatcaggca | 1440 |
| ctcgttgggg | ataagtcact | ggcattttgg | ttgatggacg | ccgaaatgta | taccaacatg | 1500 |
| agtgttctga | ccccttttac | tccagttatt | gatcgtggaa | tacagcttca | caaatgatt | 1560 |
| cgactcatta | ctcacgcact | cggtggagag | ggctatctca | atttcatggg | taatgaattt | 1620 |
| gggcatccgg | aatggctaga | cttcccaaga | aaggggaata | tgagagcta | ccattatgcc | 1680 |
| agaaggcagt | tcattttaac | tgatgatgac | cttcttcgct | acaagttcct | aaataacttt | 1740 |
| gacagggata | tgaataaatt | ggaagaaaga | tgtgttggc | tttccgctcc | ccaggcattt | 1800 |
| gtgagtgaaa | agcatgaagg | caataaggtc | atcgcttttg | agagagcagc | tcttctttt | 1860 |
| attttcaact | tccatccaag | caagagctac | accaattaca | gagtcggaac | gacattgcca | 1920 |
| gggaaattca | aaattgtgct | agattccgac | gcagcggaat | atggaggaca | ccagagattg | 1980 |
| gaccacaata | ccgatttctt | ttctgagcct | tatgagcata | tgagcgtcc | ctcttcyctt | 2040 |
| ttggtgtaca | ttccaagccg | agtggccctc | attcttcaga | acgtggatcc | gcccaactga | 2100 |

<210> SEQ ID NO 29
<211> LENGTH: 2100

<212> TYPE: DNA
<213> ORGANISM: Equus caballus

<400> SEQUENCE: 29

| | | | | | |
|---|---|---|---|---|---|
| atggcggcgc | cggcggctcg | ggccgacggc | tccgacgcgg | cgctggcggc | ggccctggcg | 60 |
| gacgtgcccg | acctgggccg | ccttctggag | gtcgacccgt | acctgaagcc | ctacgccccg | 120 |
| gacttccagc | gcaggtataa | ccggtttagc | cagactttgg | acaacattgg | aaagaatgaa | 180 |
| ggtggtattg | acaagttttc | cagaggttat | gaatcatttg | gcgtccacag | atgtgctgac | 240 |
| gggggcttat | actgcaaaga | gtgggccccg | ggagcagaag | gagttttttct | tactggagac | 300 |
| ttcaatgatt | ggaatccatt | ttcgtaccca | tacaaaaaac | tggattatgg | aaaatgggat | 360 |
| ctgtatatcc | caccaaagcc | taataaatcc | ctcctggtac | cgcatggatc | caaattaaag | 420 |
| gtagttatta | ggagtaaaag | tggagagatc | ttgtatcgta | tttcaccgtg | ggcgaagtat | 480 |
| gtggttcgtg | aaagtggtaa | tgtgaattat | gattggatac | actgggatcc | agaacagcca | 540 |
| tataaattta | agcattccag | accaaagaag | ccaagaagtc | taagaattta | tgaatctcat | 600 |
| gtgggaattt | cttcccatga | aggaaaaata | gcttcttata | acattttac | atgcaacgta | 660 |
| ctaccaagaa | tcaaaggcct | tggatacaac | tgcattcaga | tgatggcaat | catggagcac | 720 |
| gcttactacg | ccagttttgg | ttaccagatc | acaagcttct | ttgcagcgtc | aagccgttac | 780 |
| ggaacacctg | aagagctaaa | agaattggtt | gacaccgctc | actcaatggg | tattacagtc | 840 |
| ctcttagatg | tagtgcacag | ccatgcctcc | aaaaattcag | aagatggatt | gaatatgttt | 900 |
| gatgggacag | actcctgtta | ttttcattct | ggacctagag | ggactcatga | tctttgggat | 960 |
| agtcgattgt | ttatctactc | cagctgggaa | gttttaagat | tccttctgtc | aaacataaga | 1020 |
| tggtggtttg | aagaatatgg | ctttgatggg | tttcgttttg | atggtgttac | atccatgctc | 1080 |
| tatcatcacc | atggaattgg | tgcaagcttt | tcaggtgatt | accatgaata | ttttggactc | 1140 |
| caagtagatg | aagacgcctt | gacttatctc | atgctggcca | atcatttggt | tcacacgttg | 1200 |
| tatccggatt | ctatcacaat | agctgaggat | gtctcaggaa | tgccggctct | gtgttctccg | 1260 |
| atttcccagg | gaggggtgg | cttttgactat | agattagcca | tggcaattcc | ggacaaatgg | 1320 |
| atccagctag | ttaaggagtt | taaagatgaa | gattggaaca | tgggcaacat | agtgtacact | 1380 |
| ctcacaaaca | gacgccacct | tgaaaagtgc | atcgcttatg | cagagagcca | tgatcaggca | 1440 |
| ctcgttgggg | ataagtcact | ggcattttgg | ttgatggacg | ccgaaatgta | taccaacatg | 1500 |
| agtgttctga | ccccttttac | tccagttatt | gatcgtggaa | tacagcttca | caaaatgatt | 1560 |
| cgactcatta | ctcacgcact | cggtggagag | ggctatctca | atttcatggg | taatgaattt | 1620 |
| gggcatccgg | aatggctaga | cttcccaaga | aaggggaata | tgagagcta | ccattatgcc | 1680 |
| agaaggcagt | tcatttaac | tgatgatgac | cttcttcgct | acaagttcct | aaataacttt | 1740 |
| gacagggata | tgaataaatt | ggaagaaaga | tgtggttggc | tttccgctcc | ccaggcatttt | 1800 |
| gtgagtgaaa | agcatgaagg | caataaggtc | atcgcttttg | agagagcagc | tcttcttttt | 1860 |
| attttcaact | tccatccaag | caagagctac | accaattaca | gagtcggaac | gacattgcca | 1920 |
| gggaaattca | aaattgtgct | agattccgac | gcagcggaat | atgaaggaca | ccagagattg | 1980 |
| gaccacaata | ccgatttctt | ttctgagcct | tatgagcata | tgagcgtcc | ctcttcyctt | 2040 |
| ttggtgtaca | ttccaagccg | agtggccctc | attcttcaga | acgtggatcc | gcccaactga | 2100 |

<210> SEQ ID NO 30
<211> LENGTH: 1121
<212> TYPE: DNA

<213> ORGANISM: Equus caballus
<220> FEATURE:
<221> NAME/KEY: misc_feature
<222> LOCATION: (1)...(1121)
<223> OTHER INFORMATION: n = A, T, G or C

<400> SEQUENCE: 30

| | | | | | |
|---|---|---|---|---|---|
| ttttgtaagc | gtatggagcc | ctctagtggt | gattbnttta | aaggagtctc | acagtgaggc | 60 |
| cagaactgtt | ggaacatgga | actagtctcc | ccagagccgg | gagagttata | aagataactg | 120 |
| caactttaag | caaacgtgac | actgcgtcat | gtccctttgc | cacagtgaca | ctgcgctcag | 180 |
| tatttctttc | agttgcactg | acatgcttgt | gttgacgtag | gtgtacattc | caagccgagt | 240 |
| ggccctcatt | cttcagaacg | tggatccgcc | caactgaaga | gacctggctt | cagctccact | 300 |
| ggaggaagac | tgtgccttgc | tccccgtcct | caatgtcgca | gagcttatga | tgtgtacgct | 360 |
| tctcaaaata | cggttgtcta | gccaaaatgt | cagatgtctg | aaattcagta | ttgctctatg | 420 |
| caaatgatgg | tcaaactttt | aagaagtggg | cggaggatat | ttttgaaatt | tcagggaccc | 480 |
| tggactatat | tttccaagca | tctgagcagt | taggatcctc | aaacaaagca | ttatacataa | 540 |
| tgtctttaaa | caacattgct | ctcctggctt | taagttcaaa | tttgaattgt | gtcgtgtatg | 600 |
| gttatttctg | ttgaatgtag | acagtatttt | ttaaggtgga | tatttggtgg | ctttatttgt | 660 |
| tctaatatct | cttggtctga | attacanagt | accaagattg | ttactgtgtt | tnaaaaattg | 720 |
| tgtttaggaa | tactgtaata | aatagtaata | taagaagtaa | taaatagtaa | tataagaata | 780 |
| agagttgtat | caaaggtagc | ataaaagtta | ttatcgatga | actcccctat | gcctcatttt | 840 |
| gcataagnnn | catcatgtga | tctcttgttc | acttagtatc | ttggtagatg | caggatatca | 900 |
| cagtctatcc | aaaggcctga | attggtaatt | ttaacatttc | agaaaatgnc | ttttacttag | 960 |
| aatcaataaa | aaaaaatttg | caaattgcct | ttgctacaaa | tggctatttt | gctgtactat | 1020 |
| tatgggatt | gatttacaat | gaatattaaa | atgccttatc | acaattctga | tactttcccc | 1080 |
| acgtatatgc | atatgtgcac | aaggacgagg | aggcatggcg | a | | 1121 |

<210> SEQ ID NO 31
<211> LENGTH: 609
<212> TYPE: DNA
<213> ORGANISM: Equus caballus

<400> SEQUENCE: 31

| | | | | | |
|---|---|---|---|---|---|
| ggctggggag | cggtcctcac | attctcaacg | gtatcgctac | agtcacacta | gactgttgcc | 60 |
| ctcactggga | gtttactcga | tccgtcggaa | acaccgccct | aacagcaaca | aattcgcgga | 120 |
| acttctagaa | gaaaggtccc | tcccaagaaa | gccagctcag | ccactcgaag | gggctgccgc | 180 |
| cgcgggaggc | gccgcaggcg | gacgagcgga | ggggcgccgg | ccggctcggg | gagggcaggc | 240 |
| ggccgcgccg | ggaggggggc | ggccgggccc | agtgcgcgc | ggcgggcggg | cgccgcctcc | 300 |
| tccgccggcc | gctcctcccc | gccgcggggg | cagggcagcg | ccgcgctcgc | gctataaagg | 360 |
| gccccgggcc | gcagccgctc | gcctcggcgt | ccctcggctc | cgccctcgcg | ccggccactc | 420 |
| cgcggagctc | gttcccgctc | gagcggctcg | ggcctcggct | actcgggctg | cggccgaaga | 480 |
| tggcggcgcc | ggcggctcgg | gccgacggct | ccgacgcggc | gctggcggcg | gccctggcgg | 540 |
| acgtgcccga | cctgggccgc | cttctggagg | tcgacccgta | actgaagccc | tacgccccgg | 600 |
| acttccagc | | | | | | 609 |

US 7,129,049 B2

METHOD OF DETECTING EQUINE GLYCOGEN STORAGE DISEASE IV

STATEMENT REGARDING FEDERALLY SPONSORED RESEARCH OR DEVELOPMENT

Work relating to this application was supported by grants from the National Institutes of Health T32 AR007612. The government may have certain rights in the invention.

BACKGROUND OF THE INVENTION

Glucose, a major source of energy for the body, is stored in the form of glycogen. It is later released with the help of enzymes. Glycogen is found mainly in liver and muscle cells, while the kidneys and intestines are minor storage sites. The underlying problem in all of the Glycogen Storage Diseases (GSD) is the use and storage of glycogen. Currently, there are about eleven known types of GSD that affect humans. All of the different types of GSD, also referred to as glycogenoses, result in the body not being able to produce sufficient glucose in the blood stream or to utilize glucose as a source of energy. Almost all forms of GSD occur when a child inherits the affected gene from both parents (autosomal recessive inheritance), each of whom is a carrier but may not be affected by GSD themselves.

Glycogen Storage Disease Type IV (also referred to as GSD IV, brancher deficiency, Andersen disease or amylopectinosis) represents 0.3% of all glycogenoses. In the human, it is a rapidly progressive disorder leading to terminal liver failure unless liver transplantation is performed. In Norwegian Forest Cats, GSD IV is fatal, primarily affecting striated muscles and the nervous system, while the liver remains relatively unaffected (Fyfe et al. 1992; Fyfe et al. 1994). A fatal neonatal disease closely resembling GSD IV has recently been reported in the American Quarter Horse, wherein clinical signs varied from stillbirth, transient flexural limb deformities, seizures, and respiratory or cardiac failure to persistent recumbency (Render et al. 1999; Valberg et al. 2001; Sponseller et al. 2002).

Thus, GSD IV is a clinically heterogeneous disorder. It is caused by a deficiency of the glycogen branching enzyme (GBE) (EC 2.4.1.18). The deficiency leads to an accumulation of glycogen having very long outer branches. This structurally abnormal glycogen is thought to trigger the body's immune system, causing the body to actually attack the glycogen and the tissues in which it is stored. Several mutations have been reported in the gene encoding human GBE, i.e., the GBE1 gene, in patients with the classic phenotype. Mutations in human GBE1 have also been identified in patients with the milder non-progressive hepatic form of the disease. The GBE amino acid sequence shows a high degree of conservation throughout species. Human GBE1 cDNA is approximately 3 Kb in length and encodes a 702-amino acid protein. The human GBE1 gene is located on chromosome 3p 14 and consists of 16 exons spanning at least 118 kb of chromosomal DNA.

In the Norwegian Forest cat, GSD IV is caused by a 6.1 kb deletion that eliminates exon 12 of the feline GBE1 gene (Fyfe et al. 1997).

Diagnosis of GSD IV is made on the basis of an individual's symptoms, the results of a physical examination and of biochemical tests. Occasionally, a muscle or liver biopsy is required to confirm the actual enzyme defect. GBE deficiency may be a common cause of neonatal mortality in Quarter Horses that is obscured by the variety of clinical signs that resemble other equine neonatal diseases. Therefore, despite the foregoing, there is a need in the art for additional diagnostic tests for diagnosing GSD IV in horses.

SUMMARY OF THE INVENTION

The present invention provides a method for detecting the presence of a biomarker associated with equine glycogen storage disease IV (GSD IV). In one embodiment of the invention, the method involves obtaining a physiological sample from a horse, such as an American Quarter horse or related breed, wherein the sample comprises nucleic acid, and determining the presence of the biomarker. As used herein, the phrase "physiological sample" is meant to refer to a biological sample obtained from a mammal that contains nucleic acid. For example, a physiological sample can be a sample collected from an individual horse, such as including, but not limited to, e.g., a cell sample, such as a blood cell, e.g., a lymphocyte, a peripheral blood cell; a sample collected from the spinal cord; a tissue sample such as cardiac tissue or muscle tissue, e.g., cardiac or skeletal muscle; an organ sample, e.g., liver or skin; a hair sample, e.g., a hair sample with roots; and/or a fluid sample, such as blood.

The term "biomarker" is generally defined herein as a biological indicator, such as a particular molecular feature, that may affect or be related to diagnosing or predicting an individual's health. For example, in certain embodiments of the present invention, the biomarker comprises a mutant equine glycogen branching enzyme 1 (GBE1) gene, such as a polymorphic allele of GBE1 having a premature stop codon. In one embodiment, the premature stop codon is in exon 1 of GBE1. For example, the premature stop codon may be a C to A substitution at nucleotide 102 of GBE1 exon 1, or a GBE1 encoding a truncated protein having a Y to X substitution at amino acid residue 34.

The phrase "related breed" is used herein to refer to breeds that are related to the American Quarter horse. Such breed include, but are not limited to stock breeds such as the American Paint horse, the Appaloosa, and the Palomino.

"Oligonucleotide probe" can refer to a nucleic acid segment, such as a primer, that is useful to amplify a sequence in the GBE1 gene that is complementary to, and hybridizes specifically to, a particular sequence in GBE1 or to a nucleic acid region that flanks GBE1.

As used herein, the term "nucleic acid" and "polynucleotide" refers deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucl. Acids Res.,* 19:508 (1991); Ohtsuka et al., *J. Biol. Chem.,* 260:2605 (1985); Rossolini et al., *Mol. Cell. Probes,* 8:91 (1994).

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

In one embodiment of the present invention, the method also involves contacting the sample with at least one oligonucleotide probe to form a hybridized nucleic acid and amplifying the hybridized nucleic acid. "Amplifying" utilizes methods such as the polymerase chain reaction (PCR), ligation amplification (or ligase chain reaction, LCR), strand displacement amplification, nucleic acid sequence-based amplification, and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. For example, in certain embodiments of the present invention, exon 1 of the equine glycogen branched enzyme 1 gene, or a portion thereof, may be amplified by PCR. In another embodiment of the present invention, at least one oligonucleotide probe is immobilized on a solid surface.

The methods of the present invention can be used to detect the presence of a biomarker associated with equine glycogen storage disease IV (GSD IV) in a horse such as a foal, e.g., a neonatal foal or an aborted foal, one of a breeding pair of horses, e.g., the potential dam and/or sire. The horse can be alive or dead.

Further provided by the present invention is a method for diagnosing glycogen storage disease type IV (GSD-IV) in a horse, the method involving obtaining a physiological sample from the horse, wherein the sample comprises nucleic acid; and detecting the presence of a biomarker in the sample, wherein the presence of the biomarker is indicative of the disease. One embodiment of the method further involves contacting the sample with at least one oligonucleotide probe to form a hybridized nucleic acid and amplifying the hybridized nucleic acid. For example, in one embodiment, exon 1 of equine glycogen branched enzyme 1 or a portion thereof is amplified, for example, by polymerase chain reaction, strand displacement amplification, ligase chain reaction, amplification methods based on the use of Q-beta replicase and/or nucleic acid sequence-based amplification. In one embodiment of the method, the biomarker contains an equine glycogen branching enzyme 1 gene having a premature stop codon, e.g., a C to A substitution at nucleotide 102 in exon 1 of the equine glycogen branching enzyme 1 gene, or a gene encoding an glycogen branching enzyme having a Y to X substitution at amino acid residue 34. The method can be used to detect GSD IV in an American Quarter Horse, an American Paint Horse, an Appaloosa, a Palamino, or any combination thereof, e.g., a cross of any of these breeds.

Further provided by the present invention is a kit comprising a diagnostic test for detecting the presence of equine glycogen storage disease IV in a horse comprising packaging material, containing, separately packaged, at least one oligonucleotide probe capable of forming a hybridized nucleic acid with GBE1 and instructions means directing the use of the probe in accord with the methods of the invention.

BRIEF DESCRIPTION OF DRAWINGS

FIG. 1. A: Alignment of the control horse (SEQ ID NO:1) and human (SEQ ID NO:2) GBE1 amino acid sequences; B: Alignment of available mammalian GBE1 exon 1 amino acid sequences. Amino acid sequences for the control horse (SEQ ID NO:3) were translated from the cDNA obtained in this study (GenBank accession number AY505107; SEQ ID NO:27), and those for human (SEQ ID NO:5), mouse (SEQ ID NO:6), rat (SEQ ID NO:7), cat (SEQ ID NO:4) and pig (SEQ ID NO:8) were translated from accession numbers NM000158, NM028803, XM221747, AY439007, and BG835446 respectively.

FIG. 2. Equine GBE1 5' end and cDNA sequence (SEQ ID NO:9) used for mutation analysis. Nucleotide positions are numbered relative to the ATG start codon (position 1). 5' end sequence reliably obtained is provided in GenBank accession number AY505107; SEQ ID NO:27). Underlined sequences indicate the forward and reverse PCR primers. ! indicates the site of the 102 C to A mutation in codon 34, and <> indicates the exon 1–exon 2 boundary.

FIG. 3. Sequence chromatograms of nucleotides 92–108 in a PCR product from the genomic DNA of a control (SA; SEQ ID NO:10), a carrier (5B; SEQ ID NO:11) and an affected (SC; SEQ ID NO:12) horse. PCR reactions and sequencing of the products were performed as described in Materials and Methods. The arrow indicates base 102 of the PCR product.

DETAILED DESCRIPTION OF THE INVENTION

I. Definitions

An "autosomal-recessive" disorder or disease is one wherein an individual having two copies of a mutant gene are affected. The affected individual is the offspring of heterozygous carriers. Thus, a "carrier" refers to an individual who is heterozygous for a recessive, disease-causing allele. For example, if both the dam and sire of a breeding pair of horses are carriers for Glycogen Storage Disease IV (GSD IV), there is a one in four chance that their foal will be homozygous for the mutant allele and will be affected by GSD IV.

An "allele" is a variant form of a particular gene. For example, the present invention relates, inter alia, to the discovery that some alleles of the GBE1 gene cause glycogen storage disease in the American Quarter horse, in particular, GSD IV. A "GBE1 allele" refers to a normal allele of the GBE1 locus as well as an allele carrying a variation(s) that predispose a horse to develop glycogen storage disease IV. The coexistence of multiple alleles at a locus is known as "genetic polymorphism." Any site at which multiple alleles exist as stable components of the population is by definition "polymorphic." An allele is defined as polymorphic if it is present at a frequency of at least 1% in the population. A "single nucleotide polymorphism (SNP)" is a DNA sequence variation that involves a change in a single nucleotide.

The terms "protein," "peptide" and "polypeptide" are used interchangeably herein.

The invention encompasses isolated or substantially purified nucleic acid compositions. In the context of the present invention, an "isolated" or "purified" DNA molecule is a DNA molecule that, by human intervention, exists apart from its native environment and is therefore not a product of nature. An isolated DNA molecule may exist in a purified form or may exist in a non-native environment. For example, an "isolated" or "purified" nucleic acid molecule, or portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences and proteins or partial-length proteins encoded thereby are also encompassed by the present invention.

By "fragment" or "portion" of a sequence is meant a full length or less than full length of the nucleotide sequence encoding, or the amino acid sequence of a polypeptide or protein. As it relates to a nucleic acid molecule, sequence or segment of the invention when linked to other sequences for expression, "portion" or "fragment" means a sequence having, for example, at least 80 nucleotides, at least 150 nucleotides, or at least 400 nucleotides. If not employed for expressing, a "portion" or "fragment" means, for example, at least 9, 12, 15, or at least 20, consecutive nucleotides, e.g., probes and primers (oligonucleotides), corresponding to the nucleotide sequence of the nucleic acid molecules of the invention. Alternatively, fragments or portions of a nucleotide sequence that are useful as hybridization probes generally do not encode fragment proteins retaining biological activity. Thus, fragments or portions of a nucleotide sequence may range from at least about 6 nucleotides, about 9, about 12 nucleotides, about 20 nucleotides, about 50 nucleotides, about 100 nucleotides or more.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis which encode the native protein, as well as those that encode a polypeptide having amino acid substitutions. Generally, nucleotide sequence variants of the invention will have in at least one embodiment 40, 50, 60, to 70%, e.g., 71%, 72%, 73%, 74%, 75%, 76%, 77%, 78%, to 79%, generally at least 80%, e.g., 81%–84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Synthetic" polynucleotides are those prepared by chemical synthesis.

"Recombinant DNA molecule" is a combination of DNA sequences that are joined together using recombinant DNA technology and procedures used to join together DNA sequences as described, for example, in Sambrook and Russell (2001).

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, such as glycogen branching enzyme, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

A "mutant" glycogen branching enzyme (GBE) refers to the protein or fragment thereof that is encoded by a GBE1 gene having a mutation, e.g., such as might occur at the GBE1 locus of equine chromosome ECA26q12–q13. A mutation in one GBE1 allele may lead to reduced, e.g., diminished, enzymatic activity in a horse heterozygous for the allele. Reduced enzymatic activity can be determined by methods known to the art. Mutations in GBE1 may be disease-causing in a horse homozygous for the mutant GBE1 allele, e.g., a horse homozygous for a mutation leading to a non-functional gene product such as a nonsense mutation in exon 1 of GBE1, such as that designated herein as Y34X. A mutation that changes a codon from one that specifies an amino acid into one that does not is a nonsense mutation. "Somatic mutations" are those that occur only in certain tissues, e.g., in liver tissue, and are not inherited in the germline. "Germline" mutations can be found in any of a body's tissues and are inherited. The present GBE1 mutation is a germline mutation.

As is discussed herein, mutations in GBE1 result in altered enzymatic activity, e.g., reduced enzymatic activity as compared to control, as well as to a reduced amount of glycogen branching enzyme expressed as compared to control. In addition, mutations in GBE1 may result in abnormally branched glycogen, for example, that might be detected by iodine absorption spectra of isolated glycogen or PAS staining of tissue sections; abnormal polysaccharide accumulation, for example, as might be detected by PAS staining of tissue sections; and to reduced immunodetectable GBE1, for example, as might be as detected with polyclonal antibodies to a rabbit GBE protein on Western blots.

"Homology" refers to the percent identity between two polynucleotide or two polypeptide sequences. Two DNA or polypeptide sequences are "homologous" to each other when the sequences exhibit at least about 75% to 85%, at least about 90%, or at least about 95% to 98% contiguous sequence identity over a defined length of the sequences.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similarity-method of Pearson and Lipman, *Proc. Natl. Acad. Sci. USA*, 85:2444 (1988); the algorithm of Karlin and Altschul, *Proc. Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988); Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994). The ALIGN program is based on the algorithm of Myers and Miller, supra. The BLAST programs of Altschul et al., *JMB*, 215:403 (1990); *Nucl. Acids Res.*, 25:3389 (1990), are based on the algorithm of Karlin and Altschul supra.

Software for performing BLAST analyses is publicly available through the National Center for Biotechnology Information (see the world wide web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized as described in Altschul et al., *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by a BLAST program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, or at least 80%, 90%, or even at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%; at least 80%, 81%, 82%, 83%, 84%, 85%, 86%, 87%, 88%, or 89%; or at least 90%, 91%, 92%, 93%, or 94%; or even at least 95%, 96%, 97%, 98% or 99% sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2×(or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, *Proc. Natl. Acad. Sci. USA*, 82:488 (1985); Kunkel et al., *Meth. Enzymol.*, 154:367 (1987); U.S. Pat. No. 4,873,192; Walker and Gaastra, *Techniques in Mol. Biol.* (MacMillan Publishing Co. (1983), and the references cited therein. Guidance as to appropriate amino acid substitutions that do not affect biological activity of the protein of interest may be found in the model of Dayhoff et al., *Atlas of Protein Sequence and Structure* (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations."

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions that alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms."

A "host cell" is a cell which has been transformed, or is capable of transformation, by an exogenous nucleic acid molecule. Thus, "transformed," "transgenic," and "recombinant" refer to a host cell or organism into which a heterologous nucleic acid molecule has been introduced. The nucleic acid molecule can be stably integrated into the genome generally known in the art and are disclosed in Sambrook and Russell, 2001). See also Innis et al., *PCR Protocols*, Academic Press (1995); and Gelfand, *PCR Strategies*, Academic Press (1995); and Innis and Gelfand, *PCR Methods Manual*, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically includes sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

Such expression cassettes will have the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified through, for example, the use of single-stranded mutagenesis. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Genome" refers to the complete genetic material of an organism.

"Coding sequence" refers to a DNA or RNA sequence that codes for a specific amino acid sequence and excludes the non-coding sequences. For example, a DNA "coding sequence" or a "sequence encoding" a particular polypeptide, is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence. It may constitute an "uninterrupted coding sequence," i.e., lacking an intron, such as in a cDNA or it may include one or more introns bounded by appropriate splice junctions. An "intron" is a sequence of RNA that is contained in the primary transcript but that is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

The term "regulatory sequence" is art-recognized and intended to include promoters, enhancers and other expression control elements (e.g., polyadenylation signals). Such regulatory sequences are known to those skilled in the art and are described in Goeddel, Gene Expression Technology: *Methods in Enzymology*, 185, Academic Press, San Diego, Calif. (1990). It should be understood that the design of the expression vector may depend on such factors as the choice of the host cell to be transfected and/or the amount of fusion protein to be expressed.

The term DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

A control element, such as a promoter, "directs the transcription" of a coding sequence in a cell when RNA polymerase will bind the promoter and transcribe the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones having a population of daughter cells containing the exogenous DNA.

"Operably-linked" refers to the association of nucleic acid sequences on single nucleic acid fragment so that the function of one is affected by the other, e.g, an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" or "translation stop codon" or "stop codon" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. The change of at least one nucleotide in a nucleic acid sequence can result in an interruption of the coding sequence of the gene, e.g., a premature stop codon. Such sequence changes can cause a mutation in the polypeptide encoded by a GBE1 gene. For example, if the mutation is a nonsense mutation, the mutation results in the generation of a premature stop codon, causing the generation of a truncated GBE polypeptide.

II. Methods of the Invention

A. Nucleic Acids of the Invention

Sources of nucleotide sequences from which the present nucleic acid molecules can be obtained include any prokaryotic or eukaryotic source. For example, they can be obtained from a mammalian, such as an equine, cellular source. Alternatively, nucleic acid molecules of the present invention can be obtained from a library, such as the CHORI-241 Equine BAC library or the BAC library developed at INRA, Centre de Recherches de Jouy, Laboratoire de Génétique biochimique et de Cytogénétique, Département de Génétique animale, 78350 Jouy-en-Josas Cedex, France.

As discussed above, the terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule that is complementary or hybridizes to a sequence in a gene of interest, i.e., a nucleic acid sequence encoding an equine glycogen branching enzyme, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and in one embodiment of the invention is substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Sambrook and Russell (2001). Therefore, "recombinant DNA" includes completely synthetic DNA sequences, semisynthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Glycogen Branching Enzyme (GBE)

The present invention relates to mutations in the GBE1 gene and their use in the diagnosis of GSD IV, the diagnosis of predisposition to GSD IV, and to the detection of a mutant GBE1 allele in a horse.

Glycogen branching enzyme (also referred to as GBE; 1,4-α-D-glucan branching enzyme; 1,4-α-D-glucan 6-α-D-(1,4-α-glucano)-transferase; 1,4-α-glucan branching enzyme; Amylo-(1,4 to 1,6) Transglucosidase; and Amylo-(1,4 to 1,6) Transglycosylase) participates with glycogen synthase in the synthesis of glycogen by transferring a section of a minimum of six α-1,4-linked glycosyl units into an α-1,6 position.

The GBE enzyme protein is the product of the GBE1 gene. The enzyme has been isolated and characterized from both rabbit (Zimmerman and Gold, 1983) and rat (Sato and Sato, 1980). The human GBE1 has been sequenced, but the human protein has not been isolated. Sequences from the cat gene, and partial sequences from dog and pig, are also available.

Sequence analysis indicates that glycogen branching enzyme shows a high degree of conservation throughout the animal and plant kingdom (Moses and Parvari, 2002). The protein contains two highly conserved domains with sequence similarity to isoamylase N-terminal and α-amylase. This comparison enables the recognition of the conserved amino acids that are important for the enzyme activity. Indeed, all the polymorphic sites in the human gene are located within the non-conserved sequences, whereas the mutations affecting enzyme activity reside in the conserved regions (Moses and Parvari, 2002). The branching activity of the enzyme is essential for effective packing and degradation of the stored glycogen. The genetic deficiency of the enzyme results in the accumulation in various tissues of an abnormal glycogen with fewer branch points (3.5% instead of 6.7%), more 1,4 linked glucose units and longer outer branches resulting in an amylopectin-like structure (Thon et al., 1993). These deposits are strongly periodic acid-Schiff (PAS) positive, and they are only partially digested by diastase; the iodine spectra of the material show an abnormally high absorption maxim (Herrick et al., 1994).

Glycogen branching enzyme is assayed either by measuring its stimulatory effect on glycogen phosphorylase's synthetic activity in polymerizing glucose from glucose-1-phosphate (Brown and Brown, 1966) or using glycogen synthase as the indicating enzyme and [$^{14}$C]UDP-glucose as substrate (Brown, 1985). Both assays are indirect and not suitable for quantitation of residual branching activity (Chen, 2001). In Andersen disease, GBE deficiency can usually be demonstrated in liver, leukocytes, erythrocytes and fibroblasts (Howell et al., 1971; Shin et al., 1988). On the other hand, normal leukocyte GBE activity was detected in patients with cardioskeletal myopathy (Ferguson et al., 1983; Pellissier et al., 1981).

B. Nucleic Acid Amplification Methods

According to the methods of the present invention, the amplification of DNA present in a physiological sample may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification (Kwoh et al., *Proc. Natl. Acad. Sci. USA*, 86, 1173–1177 (1989)), self-sustained sequence replication (or "3SR") (Guatelli et al., *Proc. Natl. Acad. Sci. USA*, 87, 1874–1878 (1990)), the Qβ replicase system (Lizardi et al., *Biotechnology*, 6, 1197–1202 (1988)), nucleic acid sequence-based amplification (or "NASBA") (Lewis, *Genetic Engineering News*, 12, 1 (1992)), the repair chain reaction (or "RCR") (Lewis, supra), and boomerang DNA amplification (or "BDA") (Lewis, supra).

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques (see generally Walker et al., *Proc. Natl. Acad. Sci. USA*, 89, 392–396 (1992); Walker et al., *Nucleic Acids Res.*, 20, 1691–1696 (1992)). For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. See, e.g., Weiss, *Science*, 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

In one embodiment of the invention, each exon of the GBE1 gene is amplified by PCR using primers based on the known sequence. The amplified exons are then sequenced using automated sequencers. In this manner, the exons of the GBE1 gene from horses suspected of having GSD-IV in their pedigree are sequenced until a mutation is found. Examples of such mutations include those in exon 1 of the GBE1 DNA. For example, one mutation is the C to A substitution at nucleotide base 102 in exon 1. Using this technique, additional mutations causing equine GSD-IV can be identified.

According to the diagnostic method of the present invention, alteration of the wild-type GBE1 locus is detected. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Point mutational events may occur in regulatory regions, such as in the promoter of the gene, leading to loss or diminution of expression of the mRNA. Point mutations may also abolish proper RNA processing, leading to loss of expression of the GBE1 gene product, or to a decrease in mRNA stability or translation efficiency.

If only a single allele is mutated, the horse is a heterozygous carrier of GSD-IV. If both alleles are mutated, the horse is predisposed to or has GSD-IV. The finding of GBE1 mutations thus provides both diagnostic and prognostic information.

Additional diagnostic techniques that are useful in the methods of the invention include, but are not limited to direct DNA sequencing, PFGE analysis, allele-specific oligonucleotide (ASO), dot blot analysis and denaturing gradient gel electrophoresis, and are well known to the artisan.

There are several methods that can be used to detect DNA sequence variation. Direct DNA sequencing, either manual sequencing or automated fluorescent sequencing can detect sequence variation. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments that have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). A review of currently available methods of detecting DNA sequence variation can be found in a review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

Detection of point mutations may be accomplished by molecular cloning of the GBE1 allele(s) and sequencing the allele(s) using techniques well known in the art. Alternatively, the gene sequences can be amplified directly from a genomic DNA preparation from equine tissue, using known techniques. The DNA sequence of the amplified sequences can then be determined.

There are six well known methods for a more complete, yet still indirect, test for confirming the presence of a mutant allele: 1) single stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOS) (Conner et al., 1983); 5) the use of proteins which recognize nucleotide mismatches, such as the *E. coli* mutS protein (Modrich, 1991); and 6) allele-specific PCR (Rano & Kidd, 1989). For allele-specific PCR, primers are used which hybridize at their 3' ends to a particular GBE1 mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Other techniques for detecting insertions and deletions as known in the art can be used.

In the first three methods (SSCA, DGGE and RNase protection assay), a new electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the horse wild-type GBE1 gene coding sequence. The riboprobe and either mRNA or DNA isolated from the tumor tissue are annealed (hybridized) together and subsequently digested with the enzyme RNase A that is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the GBE1 mRNA or gene but can be a segment of either. If the riboprobe comprises only a segment of the GBE1 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization.

Nucleic acid analysis via microchip technology is also applicable to the present invention. Several papers have been published that use this technique. Some of these are Hacia et al., 1996; Chee et al., 1996; Lockhart et al., 1996; Lipshutz et al., 1995.

DNA sequences of the GBE1 gene that have been amplified by use of PCR may also be screened using allele-specific probes. These probes are nucleic acid oligomers, each of which contains a region of the GBE1 gene sequence harboring a known mutation. For example, one oligomer may be about 30 nucleotides in length, corresponding to a portion of the GBE1 gene sequence. By use of a battery of such allele-specific probes, PCR amplification products can be screened to identify the presence of a previously identified mutation in the GBE1 gene. Hybridization of allele-specific probes with amplified GBE1 sequences can be performed, for example, on a nylon filter. Hybridization to a particular probe under stringent hybridization conditions indicates the presence of the same mutation in the tissue as in the allele-specific probe.

Alteration of GBE1 mRNA expression can be detected by any technique known in the art. These include Northern blot analysis, PCR amplification and RNase protection. Diminished mRNA expression indicates an alteration of the wild-type GBE1 gene. Alteration of wild-type GBE1 genes can also be detected by screening for alteration of wild-type GBE1 protein. For example, monoclonal antibodies immunoreactive with GBE1 can be used to screen a tissue. Lack of cognate antigen would indicate a mutation. Antibodies specific for products of mutant alleles could also be used to detect mutant GBE1 gene product. Such immunological assays can be done in any convenient formats known in the art. These include Western blots, immunohistochemical assays and ELISA assays. Any means for detecting an altered GBE1 protein can be used to detect alteration of wild-type GBE1 genes. Functional assays, such as protein binding determinations, can be used. In addition, assays can be used that detect GBE1 biochemical function. Finding a mutant GBE1 gene product indicates alteration of a wild-type GBE1 gene.

Mutant GBE1 genes or gene products can be detected in a variety of physiological samples collected from a horse. Examples of appropriate samples include a cell sample, such as a blood cell, e.g., a lymphocyte, a peripheral blood cell; a sample collected from the spinal cord; a tissue sample such as cardiac tissue or muscle tissue, e.g., cardiac or skeletal muscle; an organ sample, e.g., liver or skin; a hair sample, especially a hair sample with roots; a fluid sample, such as blood.

The methods of diagnosis of the present invention are applicable to any disease in which GBE1 has a role. The diagnostic method of the present invention is useful for veterinarians, so they can decide upon an appropriate course of treatment.

C. Oligonucleotide Probes

As noted above, the method of the present invention is useful for detecting the presence of a polymorphism in equine DNA, in particular, the presence of a C to A nucleotide substitution at position 102 in exon 1 of the coding sequence of equine GBE1 (SEQ ID NO:28). By way of comparison, the coding sequence of equine GBE1 from a control horse is provided in SEQ ID NO:29. This substitution results in the conversion of a TAC codon, which encodes tyrosine, to TAA, which represents a premature stop codon (see FIGS. 2 and 3). This premature stop codon corresponds to a Y to X substitution at amino acid residue 34 in SEQ ID NO: 1 (Y34X).

Primer pairs are useful for determination of the nucleotide sequence of a particular GBE1 allele using PCR. The pairs of single-stranded DNA primers can be annealed to sequences within or surrounding the GBE1 gene on equine chromosome ECA26q12-q13 in order to prime amplifying DNA synthesis of the GBE1 gene itself. A complete set of these primers allows synthesis of all of the nucleotides of the GBE1 coding sequences, i.e., the exons. The set of primers preferably allows synthesis of both intron and exon sequences. Allele-specific primers can also be used. Such primers anneal only to particular GBE1 mutant alleles, and thus will only amplify a product in the presence of the mutant allele as a template.

The first step of the process involves contacting a physiological sample obtained from a horse, which sample contains nucleic acid, with an oligonucleotide probe to form a hybridized DNA. The oligonucleotide probes that are useful in the methods of the present invention can be any probe comprised of between about 4 or 6 bases up to about 80 or 100 bases or more. In one embodiment of the present invention, the probes are between about 10 and about 20 bases.

The primers themselves can be synthesized using techniques which are well known in the art. Generally, the primers can be made using oligonucleotide synthesizing machines which are commercially available. Given the sequence of the GBE1 coding sequence as set forth in Genbank accession number AY505107 (SEQ ID NO:27), design of particular primers is well within the skill of the art.

Oligonucleotide probes may be prepared having any of a wide variety of base sequences according to techniques that are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 7deaza-guanine 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, β,D-galactosylqueosine, 2'-O-methylguanosine, inosine, N6-isopentenyladenosine, 1-methyladenosine, 1-methylpseeudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β,D-mannosylqueosine, 5-methloxycarbonylmethyluridine, 5-methoxyuridine, 2-methyltio-N-6-isopentenyladenosine,N-((9-β-D-ribofuranosyl-2-methylthiopurine-6-yl)carbamoyl)threonine, N-((9-β-D-ribofuranosylpurine-6-yl)N-methyl-carbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-Methylurdine, N-((9-.beta.-D-ribofuranosylpurine-6-yl)carbamoyl)threonine, 2'-O-methyl-5-methyluridine, 2'-O-methylurdine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonotlioates, phosphoroinorpholidates, phosphoropiperazidates and phosplioramidates (for example, every other one of the internucleotide bridging phosphate residues may be modified as described). The oligonucleotide may be a "peptide nucleic acid" such as described in Nielsen et al., *Science,* 254, 1497–1500 (1991).

The only requirement is that the oligonucleotide probe should possess a sequence at least a portion of which is capable of binding to a known portion of the sequence of the DNA sample.

It may be desirable in some applications to contact the DNA sample with a number of oligonucleotide probes having different base sequences (e.g., where there are two or more target nucleic acids in the sample, or where a single target nucleic acid is hybridized to two or more probes in a "sandwich" assay).

The nucleic acid probes provided by the present invention are useful for a number of purposes. The probes can be used to detect PCR amplification products. They may also be used to detect mismatches with the GBE1 gene or mRNA using other techniques.

D. Hybridization Methodology

The DNA (or nucleic acid) sample may be contacted with the oligonucleotide probe in any suitable manner known to those skilled in the art. For example, the DNA sample may be solubilized in solution, and contacted with the oligonucleotide probe by solubilizing the oligonucleotide probe in solution with the DNA sample under conditions that permit hybridization. Suitable conditions are well known to those skilled in the art. Alternatively, the DNA sample may be solubilized in solution with the oligonucleotide probe immobilized on a solid support, whereby the DNA sample may be contacted with the oligonucleotide probe by immersing the solid support having the oligonucleotide probe immobilized thereon in the solution containing the DNA sample.

III. Equine Glycogen Storage Disease IV (GSD IV)

A previous report examined seven related Quarter Horse foals that died by 7 weeks of age for glycogen branching enzyme (GBE) deficiency (Valberg et al., 2001). Clinical signs in the foals varied from stillbirth, transient flexural limb deformities, seizures, and respiratory or cardiac failure to persistent recumbency. Leukopenia (in 5 of 5 foals tested) as well as high serum creatine kinase (CK; in 5 of 5 foals tested), aspartate transaminase (AST; in 4 of 4 foals tested), and gamma glutamyl transferase (GGT; in 5 of 5 foals tested) activities were present in most foals, and intermittent hypoglycemia was present in 2 foals. Gross postmortem lesions were minor, except for pulmonary edema in 2 foals. Muscle, heart, and/or liver samples from the foals contained abnormal periodic acid Schiff's (PAS)-positive globular or crystalline intracellular inclusions in amounts proportional to the foal's age at death.

Accumulation of an unbranched polysaccharide in tissues was suggested by a shift in the iodine absorption spectra of polysaccharide isolated from the liver and muscle of affected foals. Skeletal muscle total polysaccharide concentrations were reduced by 30%, but liver and cardiac muscle glycogen concentrations were normal.

Several glycolytic enzyme activities were normal, whereas GBE activity was virtually absent in cardiac and skeletal muscle, as well as in liver and peripheral blood cells of affected foals. GBE activities in peripheral blood cells of dams of affected foals and several of their half-siblings or full siblings were ~50% of controls. GBE protein in liver determined by Western blot was markedly reduced to absent in affected foals, and in a half-sibling of an affected foal, it was approximately one-half the amount of normal controls.

Pedigree analysis of the foals tested supported an autosomal recessive mode of inheritance. The affected foals have at least 2,600 half-siblings.

Comparative biochemical and histopathological evidence suggests that a heritable deficiency in the glycogen branching enzyme (GBE1) is responsible for GSD-IV in American Quarter Horses.

The complete nucleotide sequence of the control and affected foal GBE1 cDNA is described herein as SEQ ID NO:29 and SEQ ID NO:28, respectively. A C to A substitution was identified at base 102 in exon 1 of the GBE1 DNA sequence, resulting in a substitution of tyrosine with a premature stop mutation in codon 34 (Y34X). Each of the eleven affected foals tested was homozygous for the X34 allele, whereas each of their eleven available dams and sires were heterozygous for the allele. Each of the 16 control horses tested were homozygous for the Y34 allele. The previously reported phenotypic findings that included poorly branched glycogen, abnormal polysaccharide accumulation, lack of measurable GBE1 enzyme activity and lack of immuno-detectable GBE1 protein in GBE1 deficiency, coupled with the fact that there was no major difference in GBE1 mRNA levels observed between affected and control foals, can be explained by a premature stop signal in codon 34 of the 699 amino acid GBE1 protein. An analysis of the foals' pedigree revealed prolific stallions with many thousands of offspring that are possible carriers of the recessive X34 allele. Defining the molecular basis of GSD IV allows for accurate DNA testing and the ability to prevent occurrence of this devastating disease in American Quarter Horses and related breeds such as American Paint Horses, Appaloosas, and Palaminos, as well as cross-bred animals of these breeds.

EXAMPLE 1

Glycogen Branching Enzyme (GBE1) Mutation Causing Fatal Glycogen Storage Disease IV in American Quarter Horse Foals Introduction Glycogen is a vital storage form of carbohydrate in many cells that is composed of straight-chain α-1,4 glucose linkages with α-1,6 branch points approximately every seven to nine residues. Glycogen synthase synthesizes the straight-chain α-1,4 glucosyl linkages from UDP-glucose, while glycogen branching enzyme (1,4-α-glucan branching enzyme; GBE1) transfers existing blocks of glucosyl residues from a growing chain to another chain to produce α-1,6 linkages. Glucose is mobilized from glycogen by the combined action of glycogen phosphorylase and debranching enzyme. Glycogen supplies in the liver are essential for maintaining blood glucose homeostasis, while cardiac and skeletal muscle glycogen is used to fuel muscle contraction. A number of glycogen storage disorders (glycogenoses) due to mutations in enzymes of glycogenolysis, glycolysis, and glycogen synthesis have been described in humans and animal species (DiMauro and Lamperti 2001; Chen 2001).

Glycogen storage disease type IV (GSD IV) is a rare, heritable disorder in humans that results in an accumulation of amylopectin within cells, particularly in the cells of the liver, muscle and/or nervous tissue (Andersen 1956; Brown and Brown 1966). The clinical manifestations of this disease vary widely in severity and range from mild, adult-onset muscle weakness to neonatal death from liver failure (DiMauro and Lamperti 2001; Chen 2001; Moses and Parvari 2002). Additional hallmarks of human GSD IV are a profound decrease in the activity of GBE1 as measured by an indirect enzymatic assay (Servedei et al. 1987; Brown and Brown 1989) and poorly branched glycogen isolated from affected tissues (Mercier and Whelan. 1970; Fyfe et al. 1992). One enigmatic aspect of GSD IV is how defects in an enzyme encoded by a single gene can create such a wide variety of clinical presentations (Moses and Parvari 2002), although the severity of the disease in some human cases can now be related to the severity of underlying GBE1 mutations (Bao et al. 1996). In Norwegian Forest Cats, GSD IV is fatal, primarily affecting striated muscles and the nervous system, while the liver remains relatively unaffected (Fyfe et al. 1992; Fyfe et al. 1994). This form of GSD IV is caused by a 6.1 kb deletion that eliminates exon 12 of the feline GBE1 gene (Fyfe et al. 1997).

A fatal neonatal disease closely resembling GSD IV has recently been reported in the American Quarter Horse (Render et al. 1999; Valberg et al. 2001; Sponseller et al. 2002). The initial clinical cases presented as late term abortion or dysfunction of skeletal muscle, cardiac muscle or liver dysfunction by 8 weeks of age. Histopathological examination revealed abnormal globular and crystalline polysaccharide in multiple tissues with little normal glycogen present on histopathological examination of multiple tissues. Further biochemical evaluation demonstrated that glycogen from affected foal liver and muscle showed a shift in the iodine absorption spectra consistent with an unbranched polysaccharide (Valberg et al. 2001). GBE1 enzyme assays from blood, muscle or liver tissue showed that affected foals had virtually no activity, while their available dams had approximately half of the control levels of GBE1 activity. GBE1 protein in liver determined by Western immunoblot was markedly reduced to absent in affected foals, and in a half-sibling was approximately half the control values (Valberg et al. 2001). Pedigree analysis was consistent with an autosomal recessive trait arising from a founder in these Quarter Horse families.

The GBE1 gene was mapped to equine chromosome 26 (ECA26q12-q13), which recently has been confirmed as a candidate gene for GSD IV by microsatellite marker allele association (Ward et al. 2003). All Quarter Horse foals affected with GSD IV were homozygous for an allele of a polymorphic microsatellite (GBEms1) isolated from a GBE1 genomic DNA clone, while a control horse population showed significant allelic variation with this marker. However, since the associated GBEms1 allele was common in the control horse population, it was not useful for molecular diagnostic purposes.

The present invention describes a semi-quantitative determination of the level of GBE1 mRNA transcription in control and GSD IV affected horses, the complete cDNA sequence for this gene, and the identification of a nonsense mutation that appears to explain the clinical, biochemical, and genetic features of equine GSD IV.

Materials and Methods

Acquisition of family and control horse tissues. Samples from foals with GSD IV deficiency were procured from submissions by referring veterinarians to the Neuromuscular Disease Diagnostic Laboratory at the University of Minnesota College of Veterinary Medicine. Affected foals evaluated for this study were designated: KH, MU1, MU2, MK, CA, KD, NA, IA, IN, MO and AL (Valberg et al. 2001). Blood samples for DNA isolation were collected in EDTA tubes from KD, MU, IA, IN, MO AL and the dams of NA, KD, MK, MU1, MU2, IA, MO and AL foals, as well as a half-sibling of foals KD, IA, AL and one full sibling of foal MK. Hair samples for the sires of MO, MK, KH, KD, MU2 and IN and half siblings of MK and MO were generously provided by Dr. Cecilia Penedo at the Veterinary Genetics Laboratory University of California Davis with permission from the American Quarter Horse Association. Specimens of skeletal muscle, liver and cardiac tissue were frozen in liquid nitrogen immediately after death from foals KD and KH and used to obtain cDNA sequence by RT-PCR as well as for use in the semi-quantitative RT-PCR. Control DNA was isolated from the blood of 16 healthy adult Quarter Horses. Specimens of skeletal muscle, lymphocytes, liver, spinal cord and cardiac tissue for use in RT-PCR were also frozen in liquid nitrogen immediately after death of a Quarter Horse from the University of Minnesota Veterinary Teaching Hospital who died of causes unrelated to GSD IV.

Clinical and biochemical criteria for inclusion as GSD IV cases. The population of affected foals in this study had a variety of clinical signs (Table 1). They were categorized as GSD IV affected based on two or more of the following criteria (Valberg et al. 2001): (i) clinical signs consistent with liver and/or muscular disease resulting in death by the age of 5 months; (ii) pathological finding of abnormal polysaccharide along with an absence of normal glycogen staining visualized with Periodic Acid Schiff's (PAS) staining in cardiac or skeletal muscle specimens; (iii) absence of GBE1 activity in red blood cells, muscle, and/or liver; and (iv) a dam with half normal levels of GBE1 activity in the peripheral blood cells.

TABLE 1

Clinical description of GSD IV foals

| Foal | Clinical signs | Related horses available for study |
|---|---|---|
| KH | Premature birth; hospitalized, required mechanical ventilation, euthanized at 3 days of age due to seizures. | sire |
| MU1 | Normal gestation; hospitalized at 1 day of age with weakness, failure to suckle, stabilized and discharged at 3 days of age, died suddenly following exercise at 4 days of age. | half-sib |
| MU2 | Aborted at 8 months gestation. Half sibling of MU1 | sire, half-sib |
| MK | Normal gestation; hospitalized at 1 week of age with flexural limb deformities and persistent weakness. Stabilized and discharged. Died suddenly at 4 weeks of age. | dam, sire, full sib |
| CA | Normal gestation; treated at 2 weeks of age for persistent weakness, patent urachus, diarrhea. Cardiac murmur detected. Foal died suddenly at 5 weeks of age. | none available |
| KD | Normal gestation; hospitalized at 1 day of age for weakness, seizures, and flexural limb deformity. Stabilized and discharged at 4 weeks of age, relapsed with seizures and hypoglycemia. Euthanized at 5 weeks of age due to persistent muscle weakness. | sire, half-sib |
| NA | Premature birth at 318 days; treated for weakness and flexural limb deformities; improved over 2 weeks, became weaker over the next 3 weeks. Euthanized at 5 weeks of age due to persistent weakness. | sire |
| IA | Premature birth at 316 days; weak, difficulty rising, tachypnea and tachycardia. Euthanized at 8 weeks. | dam, half-sib |
| IN | Seizures, weakness, tachypnea; sudden death at 18 weeks. | sire |
| MO | Required assistance to stand since birth. Unable to suckle. Euthanized at 4 days of age. | dam, sire |
| AU | Weak at birth, patent urachus, hypoglycemic seizures, cardiac arrythmia, muscle weakness. Euthanized at 9 weeks of age | sire |
| 11 total | | 11 parents, 5 sibs/half-sibs |

Equine GBE1 cDNA sequence by RT-PCR. cDNA sequence encompassing over 90% of the coding sequence of the equine GBE1 gene was obtained by RT-PCR. In brief, mRNA was isolated from skeletal muscle and liver tissues using the Invitrogen Micro-FastTrack 2.0 kit. cDNA was prepared using the Invitrogen Superscript II RT kit with random hexamers as primer. PCR primers to amplify the GBE1 cDNA were initially derived from the human GBE1 mRNA sequence (Thon et al. 1993). Once equine sequence was derived from these PCR products, horse specific primers (Table 2) were developed to obtain the majority of the cDNA sequence. PCR products were resolved on 1% agarose gels, purified with Qiagen kits, and sequenced on an Applied Biosystems 3100 automated DNA sequencer. All DNA sequences were manually edited with Sequencher (Gene Codes Corp) and compared with Genbank entries by BLAST searches (blastn and blastx).

GBE1 BAC isolation. The partial equine GBE1 cDNA sequence was used to design the horse specific GBE1 PCR primers for exons 2 and 15 (Table 2), which were used to screen segment I of the CHORI-241 Equine BAC library, which was converted to PCR-able super-pools at Texas A & M University (Goh et al. 2003). BACs 93G22 and 4K06 were isolated by iterative PCR of superpools, plate, row and column pools, and sequences of amplicons confirmed them as containing the expected equine GBE1 exons 2 and 15, respectively. The clones were grown in 30 ml LB cultures with 25 µg/ml chloramphenicol, and BAC DNA was isolated with PsiClone Big BAC kits (Princeton Separations, PO Box 300, Adelphia, N.J. 07710). Direct sequencing of the BACs to obtain 5' and 3' end sequences of the GBE1 gene used approximately 5 µg BAC DNA, 16 µl ABI Big Dye terminator, 25 pmol primer, and 5 mM $MgCl_2$ in a volume of 40 µl. Following ethanol precipitation the sequencing reactions were run on an ABI 3100 DNA sequencer. The initial BAC 93G22 and 4K06 sequences enabled the design of PCR primers to confirm the sequences from horse genomic DNA (GenBank accession numbers AY505110 (SEQ ID NO:30) and AY505109 (SEQ ID NO:31), respectively).

TABLE 2

PCR primers used herein.

| Loci | Forward Primer | Reverse Primer | Product Size (bp) | Application |
|---|---|---|---|---|
| Horse GBE1 exons 3–7 | GAATCCATTTTCGTACCC (SEQ ID NO:13) | ACCAGGAGTCTGTCCCATC (SEQ ID NO:14) | 646 | Horse cDNA sequencing |
| Horse GBE1 exons 7–13 | CCTGAAGAGCTAAAAGAAT (SEQ ID NO:15) | CCACGATCAATAACTGGAG (SEQ ID NO:16) | 816 | Horse cDNA sequencing Semi-quantitative RT-PCR |
| Horse GBE1 exons 11–15 | GAAGATTGGAACATGGGC (SEQ ID NO:17) | GATCCACGTTCTGAAGAATG (SEQ ID NO:18) | 806 | Horse cDNA sequencing |
| Horse GLUT4 | GAGATCGCCCCCACTCAC (SEQ ID NO:19) | CTGTCAGGCGCTTCAGACTC (SEQ ID NO:20) | 263 | Semi-quantitative RT-PCR |
| Horse GBE1 exon2 | TTTAGCCAGACTTTGGACAAC (SEQ ID NO:21) | CTCTTTGCAGTATAAGCCCC (SEQ ID NO:22) | 101 | BAC screening: BAC93G22 |

TABLE 2-continued

PCR primers used herein.

| Loci | Forward Primer | Reverse Primer | Product Size (bp) | Application |
| --- | --- | --- | --- | --- |
| Horse GBE1 exon14 | AAATTGTGCTAGATTCGGAC (SEQ ID NO:23) | CAAAAGAGAAGAGGGACGCTC (SEQ ID NO:24) | 98 | BAC screening: BAC4K06 |
| Horse GBE5'UTR/exon1 | AAATTGTGCTAGATTCGGAC (SEQ ID NO:25) | TGCGCTGGAAGTCCGGGG (SEQ ID NO:26) | 267 | Mutation detection |

Semi-quantitative reverse transcription-PCR analysis of GBE1 mRNA level. cDNA from 200 mg of muscle tissue was prepared from an affected and a control horse as described above. Equal volumes of the cDNA were then transferred to separate PCR reactions that also contained primer pairs (Table 2) for segments of both the GBE1 and the GLUT4 cDNAs. In addition, the 200 µl PCR reactions contained 10× buffer (Qiagen), 1.0 mM each dNTP, 1.0 µM each primer and 2.0 units Taq DNA Polymerase (Qiagen). The PCR cycle conditions were 94° C. for 30 s, 56° C. for 30 s, 72° C. for 1 minute, with 20 µl aliquots of the PCR samples collected at the completion of cycles 15–33 as indicated in FIG. 1. The PCR products were electrophoresed on a 1% agarose gel and the cycles at which the GLUT4 and GBE1 PCR products were first detected were visually evaluated. Mutation detection. PCR primers were designed to amplify a 267 bp segment of the equine GBE1 gene containing the 5' UTR and almost all of exon 1 (Table 2). These primers were used in PCR reactions that contained HotStar-Taq DNA Polymerase (Qiagen) and a 12% solution of PCRx Enhancer Solution (Invitrogen). PCR conditions were an initial Taq activation phase of 94° C. for 20 minutes, followed by 35 cycles of 94° C. for 30 s, 58° C. for 30 s, 68° C. for 1 minute and then a final phase of 68° C. for 5 minutes. The PCR products were electrophoresed on a 1% agarose gel and DNA bands were excised and purified using the QiaQuick Gel Extraction Kit (Qiagen). Approximately 600 ng of these DNA samples, with 12 pmol of the forward primer (Table 2) and 10% DMSO were then sequenced on an Applied Biosystems 3100 automated DNA sequencer. The nucleotide at position 236 of this PCR product (corresponding to base 102 of the cDNA) was identified as C in homozygotes for the Y34 allele, A in homozygotes for the X34 allele, and N in heterozygotes.

Results

Analysis of GBE1 mRNA expression level. Semi-quantitative RT-PCR analysis was performed as an alternative to Northern blot analysis, which proved unsuccessful presumably due to low levels of expression of the GBE1 transcript. Aliquots of identically prepared skeletal muscle cDNA from both affected and control foals were used for PCR reactions that were stopped after the completion of different cycles. PCR primers for segments of the equine GBE1 and GLUT4 cDNAs were utilized for co-amplification of these targets from cDNA, with the GLUT4 used as a control to assure comparable amounts of cDNA were used for both affected and control reactions. The staining intensity of both the GLUT4 and GBE1 PCR products increased with PCR cycle number for both control and affected foal tissues. Initial detection of the GLUT4 cDNA occurred after approximately 24 PCR cycles for both affected foal and control muscle cDNA. GBE1 cDNA detection occurred at approximately 20 cycles for the affected foal and 23 cycles for the control horse (data not shown).

Control horse GBE1 cDNA and amino acid sequences. A combination of RT-PCR and genomic DNA sequencing from BAC clones was used to derive the cDNA sequence of the control horse GBE1 gene. The horse and human GBE1 cDNA sequences (beginning at the start codon and including the stop codon) are 2100 and 2109 bases long, respectively, coding for proteins of 699 or 702 amino acids (FIG. 1A). The nine additional bases in the human cDNA sequence are located just downstream from the ATG start codon. Homology of the equine GBE1 nucleotide and amino acid sequences to those of the human are 90% and 94% respectively. Alignment of the available translated GBE1 exon 1 cDNA sequences from horse, human, mouse, rat, cat and pig demonstrates that the three amino acid deletion observed in the horse sequence is also present in the cat (FIG. 1B).

Mutation detection. The partial GBE1 cDNA sequences from 3 affected foals were obtained primarily by RT-PCR. However, as for the control sequence, PCR from genomic DNA was necessary to obtain the 5' end and most of exon 1, as well as the 3' end of exon 16 and the 3' UTR. The DNA sequence from the 5' region of the horse GBE1 gene, with sites for PCR primers and landmarks is presented in FIG. 2. A consensus TATAA box is indicated at base-126 from the start codon. At position 102 of the coding sequence a C to A substitution in the affected foals results in the conversion of a TAC codon encoding tyrosine to a TAA premature stop codon (Y34X mutation). No additional polymorphisms were found in the GBE1 coding sequence from 3 other affected and control foals. However, single nucleotide polymorphisms in the 3'UTR were observed in both affected and control foals as C to G, C to T, and T to A substitutions at positions 2160, 2161, and 2191, respectively.

Genotyping assay and genotype frequencies. A PCR product derived from primers in the 5' region and exon 1 was utilized to sequence the region containing the Y34X mutation in 11 affected foals, 8 available sires, 3 dams, 4 half-sibs, and one full sib, as well as a population of 16 control Quarter Horses. DNA sequence chromatograms of the PCR product containing the mutation are shown for a control horse, a carrier, and an affected foal (FIG. 3). The figure shows that this assay was capable of identifying the C, A and C/A mixture at base 236 of the PCR product. This base corresponds to base 102 of the cDNA, and enables the genotyping of Y34 and X34 alleles in both homozygous and heterozygous conditions.

Table 3 shows the codon 34 genotyping results for all horses tested. All affected foals in the study were homozygous for the X34 allele, while all control horses examined were homozygous for the Y34 allele. In addition, all available parents of affected foals were heterozygous, while available half-sibs to the affected foals were either heterozygous or homozygous for the Y34 allele. A chi-squared test demonstrated that the number of affected foals homozygous for the X34 allele (11) is significantly different (p<0.005) than the number expected (2.75) from the mating of presumed heterozygous parents. The likelihood that our results would occur by chance was also determined from a binomial probability. Again, assuming that all sires and dams were heterozygotes, the likelihood of all ten affected offspring being homozygous for the X34 allele is $p=0.25^{11}$ or $2.4 \times 10^{-7}$.

TABLE 3

GBE1 codon 34 genotypes in horse sample populations.

| Codon 34 | Y/Y | Y/X | X/X |
|---|---|---|---|
| Affected foals | 0 | 0 | 11 |
| Control Horses | 16 | 0 | 0 |
| Parents of affected foals | 0 | 11 | 0 |
| Siblings and half-siblings of affected foals | 2 | 3 | 0 |

DNA was PCR amplified and sequenced as described in Materials and Methods to identify whether a C or A was present at base 102 of the equine GBE1 cDNA. The corresponding codon 34 genotype is indicated as Y = TAC (tyrosine) or X = TAA (stop).

Discussion

Previous studies have found that GSD IV in American Quarter Horse foals resembles the human and feline GSD IV disorders. In particular, multiple tissues contain abnormal unbranched PAS-stained polysaccharide, with little detectable GBE1 enzyme activity, and virtually no immunodetectable GBE1 protein (Fyfe et al. 1992; DiMauro and Lamperti 2001; Valberg et al. 2001; Chen 2001; Moses and Parvari 2002). The results presented herein showing GBE1 mRNA expression in both the control and GSD IV affected horse muscles indicate that the defect responsible for reduced GBE1 activity was not at the level of transcription. Rather, GBE1 mRNA levels may be upregulated in affected foal tissue. The major result of this study was the identification of a Y34X nonsense mutation in exon 1 of the equine GBE1 gene for which all affected foals were homozygous (FIGS. 3, Table 3). That the nonsense mutation occurred at codon 34 of a 699 amino acid residue protein virtually ensures that no functional GBE1 activity could be expressed in X34 homozygotes. In addition to explaining the lack of immunodetectable GBE1 protein and enzyme activity, this mutation also explains the sparsely branched glycogen isolated from affected foal tissues resulting from GBE1 deficiency in vivo (Valberg et al. 2001).

The Y34X GBE1 nonsense mutation was present in homozygous form in all affected foals and in heterozygous form in all available sires and dams, as well as several half-sibs (Table 3). This mutation therefore segregates entirely as expected for an autosomal recessive condition predicted from pedigree analysis (Valberg et al. 2001). The affected foals identified by collaborating veterinarians across the United States displayed a variety of clinical signs common in neonatal foals with septicemia or perinatal asphyxia syndrome, but all shared the distinguishing histological feature of abnormal cellular polysaccharide deposition in PAS stains, which generally increased in quantity with age of the foal (Valberg et al. 2001; Sponseller et al. 2003). The variety of potential clinical signs in foals with GSD IV presents a diagnostic challenge, and since few foals are evaluated with PAS stains at post-mortem. Thus, a very real possibility exists that a diagnosis of GSD IV is missed in affected foals.

The full-length control horse GBE1 cDNA was sequenced. The vast majority of the cDNA sequence was obtained by RT-PCR using primers based on the human sequence. The first 120 bases of the 5' end of exon 1 remained elusive despite multiple attempts at degenerate PCR primer design from ESTs of other species, the testing of several different RT-PCR and RACE kits, and the screening of a custom-made horse liver cDNA library.

An allele of a microsatellite (GBEms1) within the equine GBE1 gene was obtained. Along with another closely linked marker on equine chromosome 26 (UMNe66), GBEms1 demonstrated significant association with the GSD IV condition (Ward et al. 2003). All affected foals were homozygous for an allele of GBEms1. However, this allele was very common in the control horse population. Therefore, it was not useful as a molecular diagnostic test.

The Y34X GBE1 mutation likely arose in a founder animal with the common GBEms1 allele (Ward et al. 2003). Sequencing genomic DNA from BAC clones revealed that both the 5' UTR and exon 1 of the equine GBE1 had a high G:C content (78%) and a relatively low sequence homology to other species. Exon 1 also contains a three amino acid gap not present in human, swine or mouse GBE1 sequences, although it is present in cats (FIG. 1B). In the present example, an enhancer solution and DMSO were used in the PCR and sequencing protocols, respectively, for the horseY34X mutation identification to attempt to overcome the challenges of a high G:C content.

The clinical severity of the GSD IV phenotype in a number of human patients can be correlated with the severity of underlying GBE1 mutations, with the greatest decrease in GBE1 activity caused by a large deletion or a nonsense mutation, and an intermediate effect on GBE1 activity arising from GBE1 point mutations (Bao et al. 1996). However, there are also reports of subjects diagnosed with GSD IV who show a decreased GBE activity in some tissues, but normal levels in others (Bruno et al. 1993; Moses and Parvari 2002), as well as patients given a preliminary diagnosis of GSD IV based on histopathology and clinical assessment who show no decrease in GBE1 activity levels in the tissues tested (Pellissier et al. 1981; Green et al. 1987; de la Blanchardiere 1994).

A premature stop codon in exon 1 of the equine GBE1 gene has been identified. The premature stop codon results in knocked out enzyme activity and in the formation of poorly branched glycogen in multiple tissues.

The horse is the second animal species in which a defined GBE1 mutation has been shown to cause a condition to similar to GSD IV in humans. It also brings the number of inherited diseases in horses for which a mutation has been defined to five; including hyperkalemic periodic paralysis, overo lethal white syndrome, severe combined immunodeficiency, and junctional epidermolysis bullosa (Rudolph et al. 1992, Santschi et al. 1998, Shin et al. 1997; and Spirito et al. 2002). Examination of pedigrees containing the GSD IV foals indicates that popular Quarter Horse sires with many thousands of descendants are carriers of the X34 allele, and a high allele frequency is expected in related bloodlines of both cutting and pleasure horses. Allele specific genotyping for the Y34X GBE1 mutation enables accurate molecular testing to determine the true allele frequencies in the Quarter Horse population and help avoid late term abortions and the production of GSD IV affected foals.

REFERENCES

Andersen, *Lab. Invest.*, 5, 11–20 (1956).
Bao et al., *J. Clin. Invest.*, 97, 941–948 (1996).
de La Blanchardiere et al., *Presse Med.*, 23, 1124–1127 (1994).
Brown and Brown, *Biochem.*, 56, 725–729 (1996).
Bruno et al., *Ann. Neurol.*, 33, 88–93 (1993).
Cariello, *Human Genetics*, 42, 726 (1988).
Chee et al., *Science*, 274, 610–614 (1996).
Chen, in *The Metabolic and Molecular Bases of Inherited Disease* (Scriver C R, Beaudet A L, Sly W S, Valle D, Childs B, Kinzler K W, and Vogelstein B, eds.) McGraw-Hill Inc., New York, 8$^{th}$ Ed., 1521–1551 (2001).
Conner et al., *Proc. Natl. Acad. Sci. USA*, 80, 278–282 (1983).
Cotton et al., *Proc. Natl. Acad. Sci. USA*, 85, 4397 (1988).
DiMauro and Lamperti, *Muscle and Nerve*, 24, 984–999 (2001).
Elghanian et al., *Science*, 277, 1078–1081 (1997).
Finkelstein et al., *Genomics*, 7, 167–172 (1990).
Fyfe et al., *Pediatr. Res.*, 32, 719–725 (1992).
Fyfe et al., *Comp. Path. Bull.*, 26, 3–6 (1994).
Fyfe et al., *Am. J. Hum. Genet.*, 61, A251 (1997).
Goh et al., Hierarchical pooling and PCR screening of segment I of the CHORI 241 equine BAC library. Proceedings of the Plant & Animal Genome Conference XI, P637 (2003).
Greene et al., *Arch. Pathol. Lab. Med.*, 111, 977–982 (1987).
Grompe et al., *Proc. Natl. Acad. Sci. USA*, 86, 5855–5892 (1989).
Grompe, *Nature Genetics*, 5, 111–117, (1993).
Hacia et al., *Nature Genetics*, 14, 441–447 (1996).
Kinszler et al., *Science*, 251, 1366–1370 (1991).
Lipshutz et al., *Biotechniques*, 19, 442–447 (1995).
Lockhart et al., *Nature Biotechnology*, 14, 1675–1680 (1996).
Modrich, *Ann. Rev. Genet.*, 25, 229–253 (1991).
Moses and Parvari, *Curr. Mol. Med.*, 2, 177–188 (2002).
Newton et al., *Nuc. Acids Res.*, 17, 2503–2516 (1989).
Novack et al., *Proc. Natl. Acad. Sci. USA*, 83, 586 (1986).
Orita et al., *Proc. Natl. Acad. Sci. USA*, 86,2776–2770 (1989).
Pellissier et al., *Acta. Neuropath.*, 7 (suppl 1), 292–296 (1981).
Rano and Kidd, *Nucl. Acids Res.*, 17, 8392 (1989).
Render et al., *Vet. Pathol.*, 36, 157–60 (1999).
Rudolph et al., *Nature Genetics*, 2, 144–147 (1992).
Sambrook and Russell, *Molecular Cloning: A Laboratory Manual*, Cold Spring Harbor, N.Y.: Cold Spring Harbor Laboratory Press (3rd edition, 2001).
Santschi et al., *Mamm. Genome.*, 9, 306–309 (1998).
Sheffield et al., *Proc. Natl. Acad. Sci. USA*, 86, 232–236 (1989).
Sheffield et al., *Am. J. Hum. Genet.*, 49, 699–706 (1991).
Shenk et al., *Proc. Natl. Acad. Sci USA*, 72, 989 (1975).
Shin et al., *J. Immunol.*, 158, 3565–3569 (1997).
Spirito et al., *J. Invest. Dermatol.*, 119, 684–691 (2002).
Sponseller et al., *Equine Veterinary Education*, 15, 182–188 (2003).
Thon et al., *J. Biol. Chem.*, 268, 7509–13 (1993).
Valberg et al., *J. Vet. Intern. Med.*, 15, 572–580 (2001).
Ward et al., *Genetic Mapping of GBE1 and its Association with Glycogen Storage Disease IV in American Quarter Horses*. Cytogenet Genome Res, in press (2003).
Wartell et al., *Nucl. Acids Res.*, 18, 2699–2705 (1990).
White et al., *Genomics*, 12, 301–306, (1992).

All publications are incorporated by reference herein, as though individually incorporated by reference. The invention has been described with reference to various specific and preferred embodiments and techniques. However, it should be understood that many variations and modifications may be made while remaining within the scope of the invention.

---

What is claimed is:

1. A method for detecting the presence of equine glycogen storage disease type IV (GSD IV) in a horse, comprising: identifying in a nucleic acid sample from a horse nucleotide 102 of SEQ ID NO:28, wherein the presence of A nucleotides at nucleotide 102 in both alleles is indicative of the horse being predisposed to or has GSD IV.

2. The method of claim 1, further comprising contacting the sample with at least one oligonucleotide probe to form a hybridized nucleic acid and amplifying the hybridized nucleic acid.

3. The method of claim 2, wherein exon 1 of equine glycogen branched enzyme 1 or a portion thereof is amplified.

4. The method of claim 2, wherein the amplification of the hybridized nucleic acid is carried out by polymerase chain reaction, strand displacement amplification, ligase chain reaction, or nucleic acid sequence-based amplification.

5. The method according to claim 2, wherein at least one oligonucleotide probe is immobilized on a solid surface.

6. The method of claim 1, wherein the horse is a foal.

7. The method of claim 1, wherein the horse is one of a breeding pair.

8. The method of claim 7, wherein the horse is a dam.

9. The method of claim 7, wherein the horse is a sire.

10. The method of claim 1, wherein the horse is an American Quarter Horse, an American Paint Horse, an Appaloosa, a Palamino, or any combination thereof.

11. A method for detecting the presence of an equine glycogen storage disease type IV (GSD IV) allele in a horse, comprising identifying in a nucleic acid sample from the horse nucleotide 102 of SEQ ID NO:28, wherein the presence of an A nucleotide at nucleotide 102 in one allele is indicative of the horse being a carrier of GSD VI.

12. The method of claim 11, further comprising contacting the sample with at least one oligonucleotide probe to form a hybridized nucleic acid and amplifying the hybridized nucleic acid.

13. The method of claim 12, wherein exon 1 of equine glycogen branched enzyme 1 or a portion thereof is amplified.

14. The method of claim 12, wherein the amplification of the hybridized nucleic acid is carried out by polymerase chain reaction, strand displacement amplification, ligase chain reaction, or nucleic acid sequence-based amplification.

15. The method according to claim 12, wherein at least one oligonucleotide probe is immobilized on a solid surface.

16. The method of claim 11, wherein the horse is a foal.

17. The method of claim 11, wherein the horse is one of a breeding pair.

18. The method of claim 17, wherein the horse is a dam.

19. The method of claim 17, wherein the horse is a sire.

20. The method of claim 11, wherein the horse is an American Quarter Horse, an American Paint Horse, an Appaloosa, a Palamino, or any combination thereof.

* * * * *